United States Patent
Berger et al.

[11] 4,034,090
[45] July 5, 1977

[54] CEPHALOSPORIN DERIVATIVES

[75] Inventors: Christian Berger, Le Plessis Robinson; Daniel Farge, Thiais; Georges Gros, Bourg-la-Reine; Mayer Naoum Messer, Bièvres; Claude Moutonnier, Le Plessis-Robinson, all of France

[73] Assignee: Rhone-Poulenc Industries, Paris, France

[22] Filed: June 30, 1975

[21] Appl. No.: 592,096

[30] Foreign Application Priority Data

July 1, 1974 France .......................... 74.22867
May 22, 1975 France .......................... 75.15937
May 22, 1975 France .......................... 75.15938

[52] U.S. Cl. .......................... 424/246; 260/243 C
[51] Int. Cl.² .............. C07D 501/20; A61K 31/545
[58] Field of Search ................. 424/246; 260/243 C

[56] References Cited

UNITED STATES PATENTS 3,907,787  9/1975  Teller et al. .................. 260/243 C

*Primary Examiner*—Nicholas S. Rizzo
*Attorney, Agent, or Firm*—Stevens, Davis, Miller & Mosher

[57] ABSTRACT

New cephalosporin derivatives of the formula:

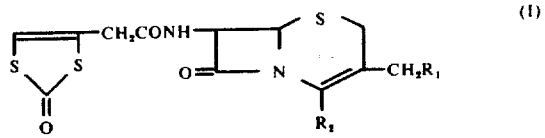

(I)

in which either (a) $R_1$ is hydrogen, acetoxy, azido or heterocyclylthio or heterocyclylcarbonylthio which is (1,3,4-thiadiazol-2-yl)-thio which is unsubstituted or substituted by straight or branched chain $C_{1-4}$ alkyl or alkoxy, straight or branched chain $C_{1-4}$ alkylthio, straight or branched chain $C_{1-4}$ alkylsulphonyl, amino or acetylamino; (1,2,3,4-tetrazol-5-yl)-thio which is unsubstituted or substituted in the 1-position by straight or branched chain $C_{1-4}$ alkyl, hydroxy straight or branched chain $C_{1-4}$ alkyl, phenyl or hydroxyphenyl, or in the 2-position by straight or branched chain $C_{1-4}$ alkyl or hydroxy straight or branched chain $C_{1-4}$ alkyl; (1,2,4-triazol-3-yl)-thio, (4-methyl-1,3-thiazol-2-yl)-thio, (3-methyl-1,2,4-thiadiazol-5-yl)-thio or (1,2,3-thiadiazol-4-yl)-carbonylthio, and $R_2$ is carboxy or a radical of the formula:

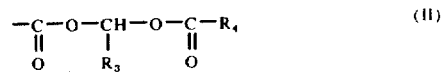

(II)

in which the radical:

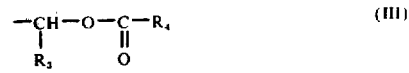

(III)

is a radical which can be easily removed enzymatically, and in which $R_3$ is hydrogen or straight or branched chain $C_{1-4}$ alkyl and $R_4$ is straight or branched chain $C_{1-4}$ alkyl or cyclohexyl; or (b) $R_1$ is a pyridinio ion and $R_2$ is a carboxylato ion, and pharmaceutically acceptable non-toxic metal salts thereof and addition salts thereof with nitrogen containing bases possess valuable antibacterial properties, showing activity against both Gram-positive and Gram-negative bacteria.

31 Claims, No Drawings

CEPHALOSPORIN DERIVATIVES

The present invention relates to cephalosporin derivatives, to their preparation and to compositions containing them.

The present invention provides cephalosporin derivatives of the formula:

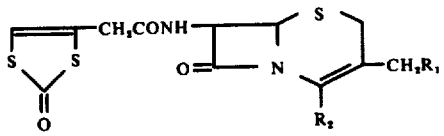

in which either (a) $R_1$ represents hydrogen, acetoxy, azido or heterocyclytho or heterocyclylcarbonylthio which is:

(1,3,4-thiadiazol-2-yl)-thio which is unsubstituted or substituted by straight or branched chain $C_{1-4}$ alkyl or alkoxy, straight or branched chain $C_{1-4}$ alkylthio, straight or branched chain $C_{1-4}$ alkylsulphonyl, amino or acetylamino;

(1,2,3,4-tetrazol-5-yl)-thio which is unsubstituted or substituted in the 1-position by straight or branched chain $C_{1-4}$ alkyl, hydroxy straight or branched chain $C_{1-4}$ alkyl, phenyl or hydroxyphenyl, or in the 2-position by straight or branched chain $C_{1-4}$ alkyl or hydroxy straight or branched chain $C_{1-4}$ alkyl;

(1,2,4-triazol-3-yl)-thio, (4-methyl-1,3-thiazol-2-yl)-thio, (3-methyl-1,2,4-thiadiazol-5-yl)-thio or (1,2,3-thiadiazol-4-yl)-carbonylthio, and $R_2$ represents carboxy or a radical of the formula:

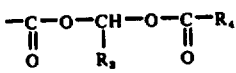

in which the radical:

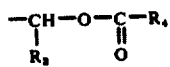

is a radical which can be easily removed enzymatically, and in which $R_3$ represents hydrogen or straight or branched chain $C_{1-4}$ alkyl and $R_4$ represents straight or branched chain $C_{1-4}$ alkyl or cyclohexyl; or (b) $R_1$ represents a pyridinio ion and $R_2$ represents a carboxylato ion, or a pharmaceutically acceptable non-toxic metal salt thereof or addition salt with a nitrogen-containing base if $R_2$ represents carboxy.

The compounds of the present invention can be prepared, according to a further aspect of this invention, by the action of (1,3-dithiol-2-on-4-yl)-acetic acid of the formula:

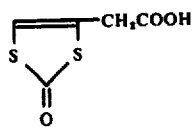

or of a derivative of this acid, such as an acid halide, anhydride or a mixed anhydride, on a cephalosporin of the formula:

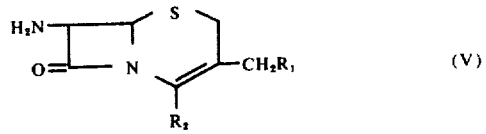

in which $R_1$ and $R_2$ are as defined above.

If the acid of formula (IV) is reacted with a cephalosporin of formula (V) in which $R_2$ represents a carboxy radical, it is preferable to protect the carboxy radical of the cephalosporin of the formula (V) beforehand by an easily removable group, such as a tertio butyl radical. In general, the reaction between the acid of formula (IV) and the cephalosporin of formula (V) is carried out in an organic solvent such as dimethylformamide, in the presence of a condensation agent such as dicyclohexylcarbodiimide, at a temperature of from 0° to 40° C, followed by removal of the group which protects the carboxy radical, for example by scission in an acid medium.

If the compound of formula (IV) is an acid halide, anhydride or a mixed anhydride, the protection of the carboxy radical of the cephalosporin of the formula (V) is not essential. However, it is possible to use a cephalosporin of the formula (V) of which the carboxy radical has been protected beforehand by an easily removable group, such as a 2,2,2-trichloroethyl radical, which can be subsequently removed by zinc in acetic acid. In general, the reaction is carried out in an organic solvent such as chloroform in the presence of an acid acceptor such as a nitrogen-containing organic base, such as triethylamine, or in an aqueous-organic medium in the presence of an alkaline condensation agent such as sodium bicarbonate, and, where necessary, the radical which protects the acid group is then removed.

If, in the cephalosporin of formula (V), $R_2$ represents a radical of the formula (II), the reaction is generally carried out in an organic solvent such as dimethylformamide in the presence of a condensation agent such as dicyclohexylcarbodiimide at a temperature of from 0° to 40° C.

The cephalosporin of the formula (V) in which $R_1$ represents a hydrogen atom and $R_2$ represents a carboxy radical is 7-amino-3-desacetoxy-cephalosporanic acid (7-ADCA), which can be obtained either from a penicillin, for example according to the process described in Belgian Pat. No. 747,382, or by desacetoxylation of a cephalosporin of the formula (V) in which $R_1$ represents an acetoxy radical and $R_2$ represents a carboxy radical, for example according to the process described in Belgian Pat. No. 779,034.

The cephalosporin of the formula (V) in which $R_1$ represents an acetoxy radical and $R_2$ is a carboxy radical is 7-amino-cephalosporanic acid (7-ACA) which can be obtained, for example, in accordance with the process described in Belgian Pat. No. 615,955 or in U.S. Pat. No. 3,239,394.

The cephalosporins of the formula (V) in which $R_1$ is as defined above except that it does not represent a hydrogen atom or an acetoxy radical, and in which $R_2$ represents a carboxy radical, or $R_1$ represents a pyridinio ion and $R_2$ represents a carboxylato ion, can be obtained, respectively, by the action of sodium azide, of a 2-thioxo-1,3,4-thiadiazoline which is unsubstituted or substituted by straight or branched chain $C_{1-4}$ alkyl or alkoxy, straight or branched chain $C_{1-4}$ alkylthio, straight or branched chain $C_{1-4}$ alkylsulphonyl, amino or acetylamino; by the action of a 5-thioxo-1,2,3,4-tetrazoline which is unsubstituted or substituted in the 1-position by straight or branched chain $C_{1-4}$ alkyl, hydroxy straight or branched chain $C_{1-4}$ alkyl, phenyl or hydroxyphenyl, or in the 2-position by straight or branched chain $C_{1-4}$ alkyl or hydroxy straight or branched chain $C_{1-4}$ alkyl; by the action of 3-thioxo-1,2,4-triazoline, of 4-methyl-2-thioxo-1,3-thiazoline, of 3-methyl-5-thioxo-1,2,4-thiadiazoline, of (1,2,3-thiadiazol-4-yl)-thiocarboxylic acid or of pyridine on a cephalosporin of the formula (V) in which $R_1$ represents an acetoxy radical and $R_2$ represents a carboxy radical.

The reaction is generally carried out by heating the reactants in an aqueous medium to a temperature of from 40° to 80° C, preferably in the presence of an activator such as an iodide or an alkali metal thiocyanate.

The cephalosporins of the formula (V) in which $R_1$ is as defined above for the compounds of formula (I) in section (a) and $R_2$ represents a radical of the formula (II) in which $R_3$ and $R_4$ are as defined above, can be prepared from a cephalosporin of the formula (V), in which $R_1$ is as defined just above and $R_2$ represents a carboxy radical, by any method known per se for the preparation of an ester from an acid without affecting the remainder of the molecule.

In general, an alkali metal salt, or a tertiary amine salt, of a cephalosporin of the formula (V), in which $R_1$ is defined as above and $R_2$ represents a carboxy radical, is reacted with a halide of the formula:

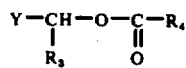

(VI)

in which $R_3$ and $R_4$ are as defined above and Y represents a halogen atom, preferably in an inert solvent such as diemthylformamide and at a temperature of from 0° to 30° C.

The acid of the formula (IV) can be obtained by the action of a potassium alkylxanthate or sodium alkylxanthate on an alkyl γ-halogenoacetoacetate followed by cyclisation, in an acid medium, of the alkyl 4-alkoxythiocarbonylthio-3-oxo-butyrate obtained.

2-Thioxo-1,3,4-thiadiazoline and the 2-thioxo-5-alkyl-1,3,4-thiadiazolines can be obtained in accordance with the method described in Japanese Pat. No. 72/07,371.

The 2-thioxo-5-alkoxy-1,3,4-thiadiazolines and 2-thioxo-5-alkylthio-1,3,4-thiadiazolines can be obtained in accordance with the method described by K. RUFENACHT, Helv. Chim. Acta, 55, 1178 (1972).

The 2-thioxo-5-alkylsulphonyl-1,3,4-thiadiazolines can be obtained by the action of phosphorus pentasulphide on a 2-oxo-5-alkylsulphonyl-1,3,4-thiadiazoline. The reaction is generally carried out under a nitrogen atmosphere under reflux in a solvent such as xylene.

The 2-oxo-5-alkylsulphonyl-1,3,4-thiadiazolines can be obtained by oxidation of 2-oxo-5-alkylthio-1,3,4-thiadiazolines. The reaction is generally carried out in the presence of hydrogen peroxide in acetic acid at a temperature of about 20° C.

The 2-oxo-5-alkylthio-1,3,4-thiadiazolines can be prepared in accordance with the method described by K. RUFENACHT, Helv. Chim. Acta, 55, 1184 (1972).

5-Amino-2-thioxo-1,3,4-thiadiazoline can be prepared in accordance with the method described by J. SANDSTROM, Acta Chem. Scand., 15, 1295 (1961).

5-Acetylamino-2-thioxo-1,3,4-thiadiazoline can be obtained in accordance with the method described in U.S. Pat. No. 2,937,182.

5-Thioxo-1,2,3,4-tetrazoline can be prepared according to the method described by M. FREUND and colleagues, Chem. Ber., 34, 3110 (1901).

The 5-thioxo-1-alkyl-1,2,3,4-tetrazolines, 5-thioxo-1-phenyl-1,2,3,4-tetrazoline and the 5-thioxo-1-hydroxyphenyl-1,2,3,4-tetrazolines can be obtained in accordance with the methods described by R. STOLLE et al., J. Prakt, Chem., 124, 261 (1930) and R. E. ORTH, J. Pharm. Sci., 52 (9), 909 (1963).

The 5-thioxo-hydroxyalkyl-1,2,3,4-tetrazolines can be obtained by addition of sodium azide to a 2-(isothiocyanatoalkoxy)-tetrahydropyrane. In general, the reaction is carried out under reflux in an organic solvent such as ethanol. The 2-(isothiocyanatoalkoxy)-tetrahydropyranes can be obtained by reacting carbon disulphide with a 2-(aminoalkoxy)-tetrahydropyrane in an alkaline medium. The reaction is generally carried out under reflux in the presence of sodium hydroxyde.

The 2-(aminoalkoxy)-tetrahydropyranes can be obtained according to the method described by V. H. MADDOX, J. Med. Chem., 8, 230 (1965).

The 5-thioxo-2-alkyl-1,2,3,4-tetrazolines and the 5thioxo-2-hydroxyalkyl-1,2,3,4-tetrazolines can be obtained by reacting aluminium bromide with a 5-benzylthio-2-alkyltetrazole or a 5-benzylthio-2 -hydroxyalkyl-tetrazole. In general, the reaction is carried out in an organic solvent such as chlorobenzene, at a temperature of about 0°C.

The 5-benzylthio-2-alkyl-tetrazoles and the 5-benzylthio-2-hydroxyalkyl-tetrazoles can be obtained by alkylation of 5-benzylthio-tetrazole. The reaction is generally carried out by reaching an alkyl halide or a halogenohydrin, in an aqueous medium, or in an organic solvent such as acetonitrile, under reflux or, in the case where the alkyl radical represents a methyl radical, by the action of diazomethane in a solvent such as ethyl ether, the reaction being carried out at a temperature of from 0° to 10° C.

3-Thioxo-1,2,4-triazoline can be prepared according to the method described in Org. Syn., 40, 99.

4-Methyl-2-thioxo-1,3-thiazoline can be prepared according to the method described by T. G. LEVI, Gazz, Chim, Ital., 61, 719 (1931).

3-Methyl-5-thioxo-1,2,4-thiadiazoline can be prepared according to the method described in Belgian Pat. No. 772,417.

(1,2,3-Thiadiazol-4-yl)-thiocarboxylic acid can be prepared according to the method described in French Pat. No. 2,181,762.

According to a further feature of the present invention, the compounds of the formula (I) in which $R_1$ is as defined above, except that it does not represent a hydrogen atom or an acetoxy radical, and $R_2$ represents a carboxy radical, or $R_1$ represents a pyridinio ion and $R_2$ represents a carboxylato ion, can also be obtained, respectively, by the action of sodium azide, of a 2-thioxo-1, 3,4-thiadiazoline as defined above in connection with the first preparation of the cephalosporins of formula (V), of a 5-thioxo-1,2,3,4-tetrazoline as defined above in connection with the first preparation of the cephalosporins of formula (V), of 3-thioxo-1,2,4-triazoline, of 4-methyl-2-thioxo-1,3-thiazoline, of 3- methyl-5-thioxo-1,2,4-thiadiazoline, of (1,2,3-thiadiazol-4-yl)-thiocarboxylic acid, or of pyridine on a compound of the formula (I) in which $R_1$ represents an acetoxy radical and $R_2$ represents a carboxy radical.

The reaction is generally carried out under the conditions described above for obtaining the cephalosporins of the formula (V), in which $R_1$ and $R_2$ are as defined above, from a product of the general formula (V) in which $R_1$ represents an acetoxy radical and $R_2$ represents a carboxy radical.

According to a feature of the present invention, the compounds of the formula (I) in which $R_1$ is as defined above and $R_2$ represents a radical of the formula (II) in which $R_3$ and $R_4$ are as defined above, can also be obtained by esterifying a compound of the formula (I), in which $R_1$ is as defined above and $R_2$ represents a carboxy radical, by any method known per se for the preparation of an ester from an acid, without affecting the remainder of the molecule.

In general, an alkali metal salt or a tertiary amine salt of a compound of the formula (I), as defined above, is reacted with a halide of the formula (VI), in which $R_3$, $R_4$ and Y are defined as above. Preferably, the reaction is carried out in an inert solvent such as dimethylformamide, and at a temperature of from 0° to 30° C.

The cephalosporin derivatives of the formula (I) can be purified by physical methods such as chromatography or crystallisation.

The cephalosporins of the formula (I) in which $R_2$ represents a carboxy radical can be converted into metal salts or into addition salts of nitrogen-containing bases in accordance with known methods. These salts can be obtained by the action of an alkali metal base or alkaline earth metal base, of ammonia or of an amine, on a cephalosporin of the formula (I), in an appropriate solvent such as in alcohol, an ether, a ketone or water, or by an exchange reaction with a salt of an organic acid. The salt formed precipitates from solution, if necessary after concentrating the solution, and is isolated by filtration, decantation or lyophilisation.

The cephalosporin derivatives of formula (I) possess particularly interesting anti-bacterial properties. They exhibit a remarkable activity in vitro and in vivo against Gram-positive and Gram-negative bacteria.

In vitro, the compounds of the formula (I) have proved active at concentrations of between 0.001 and 20 μg/cm³ against strains of *Staphylococci* which are sensitive to penicillin G (*Staphylococcus aureus* 209P and *Staphylococcus aureus* Smith) or are resistant to penicillin G (*Staphylococcus aureus* MB 9), and, at concentrations of between 0.1 and 60 μg/cm³ against *Escherichia coli*, Monod strain, and at concentrations of between 0.5 and 150 μg/cm³ against *Klebsiella pneumoniae*.

In vivo, the compounds of the formula (I) have shown themselves active against experimental infections of mice with *Staphylococcus aureus* Smith (sensitive to penicillin G) at doses of between 0.01 and 10 mg/kg per day administered orally or subcutaneously, with *Staphylococcus aureus* MB 9 (resistant to penicillin G) at doses of between 5 and 100 mg/kg administered subcutaneously, with *Escherichia coli* at doses of between 0.5 and 50 mg/kg per day administered subcutaneously or between 1 and 250 mg/kg per day administered orally, or with *Klebsiella pneumoniae* at doses of between 100 and 500 mg/kg per day administered subcutaneously.

Particularly interesting compounds of the formula (I) are those in which either $R_1$ represents a hydrogen atom, an acetoxy radical, an azido radical or a heterocyclylthio or heterocyclylcarbonylthio radical which is (1,3,4-thiadiazol-2-yl)-thio which is unsubstituted or substituted by a $C_{1-2}$ alkyl radical, methoxy, methylthio, methylsulphonyl, amino or acetylamino (1,2,3,4-tetrazol-5-yl)-thio which is unsubstituted or substituted in the 1-position by a straight or branched chain $C_{1-4}$ alkyl radical, a hydroxy $C_{1-2}$ alkyl radical or a phenyl radical, or in the 2-position by a methyl radical; (1,2,4-triazol-3-yl)-thio, (4-methyl-1,3-thiazol-2-yl)-thio, (3-methyl-1,2,4-thiadiazol-5-yl)-thio or (1,2,3-thiadiazol-4-yl)-carbonylthio and $R_2$ represents a carboxy or pivaloyloxymethoxycarbonyl radical; or $R_1$ represents a pyridinio ion and $R_2$ represents a carboxylato ion, or pharmaceutically acceptable non-toxic metal salts thereof or addition salts thereof with a nitrogen containing base if $R_2$ represents a carboxy radical.

Especially preferred compounds of the formula (I) are:

3-[(1-Methyl-1,2,3,4-tetrazol-5-yl)-thiomethyl]-2-carboxy-7-[(1,3-dithiol-2-on-4-yl)-acetamido]-8-oxo-5-thia-1-aza-bicyclo[4.2.0]oct-2-ene, 3-{[1-(2-hydroxyethyl)-1,2,3,4-tetrazol-5-yl]-thiomethyl}-2-carboxy-7-[(1,3-dithiol-2-on-4-yl)-acetamido]-8-oxo-5-thia-1-aza-bicyclo[4.2.0]oct-2-ene, 3-[(5-amino-1,3,4-thiadiazol-2-yl)-thiomethyl]-2-carboxy-7-[(1,3-dithiol-2-on-4-yl)-acetamido]-8-oxo-5-thia-1-aza-bicyclo[4.2.0]oct-2-ene, 3-[(1-methyl-1,2,3,4-tetrazol-5-yl)-thiomethyl]-2-pivaloyloxymethoxycarbonyl-7-[(1,3-dithiol-2-on-4-yl)acetamido]-8-oxo-5-thia-1-aza-bicyclo[4.2.0]oct-2-ene, 3-[(5-methyl-1,3,4-thiadiazol-2-yl)-thiomethyl]-2-carboxy-7-[(1,3-dithiol-2-on-4-yl)-acetamido]-8-oxo-5-thia-1-aza-bicyclo[4.2.0]oct-2-ene and 3-(1-pyridinio-methyl)-2-carboxylato-7-[(1,3-dithiol-2-on-4-yl)-acetamido]-8-oxo-5-thia-1-aza-bicyclo[4.2.0]oct-2-ene.

The following Examples further illustrate the present invention; percentages are by weight.

EXAMPLE 1

3-Acetoxy-7-amino-2-tertio butoxycarbonyl-8-oxo-5-thia-1-aza-bicyclo[4.2.0]oct-2-ene (13.12 g.) and dicyclohexylcarbodiimide (8.96 g.) are added to a solution of (1,3-dithiol-2-on-4-yl)-acetic acid (7.04 g.) in dimethylformamide (120 cc.). The reagents are left in contact for 2 hours with stirring at a temperature of about 20° C., and the solid obtained is filtered off. The filtrate is taken up in ethyl acetate (400 cc.) and washed twice with distilled water (600 cc.), then with a saturated solution of sodium bicarbonate (250 cc.) and with 0.5 N hydrochloric acid (500 cc.), and finally with distilled water (500 cc.). The organic phase is dried over sodium sulphate, treated with decolourising charcoal and concentrated to dryness under reduced pressure (20 mm.Hg). 3-Acetoxymethyl-2-tertio butoxycarbonyl-7-[(1,3-dithiol-2-on-4-yl)-acetamido]-8-oxo-5-thia-1-aza-bicyclo[4.2.0]oct-2-ene (18.6 g.) is obtained in an amorphous form, of which 18.5 g. is dissolved in trifluoroacetic acid (150 cc.). The reagents are left in contact for 15 minutes at a temperature of about 20° C., and then concentrated to dryness under reduced pressure (1 mm.Hg). Ethyl acetate (150 cc.) is added to the residue and thereafter a saturated solution of sodium bicarbonate is added to the suspension obtained until the pH is 8. The aqueous phase is decanted and washed with ethyl acetate (100 cc.). The aqueous solution is then acidified to pH 2 with 4 N hydrochloric acid in the presence of ethyl acetate (700 cc.). The organic phase is dried over magnesium sulphate, treated with decolourising charcoal, filtered and then concentrated to dryness under reduced pressure (20 mm.Hg). The residue (10.7 g.) is recrystallised from boiling methanol (200 cc.) to give 3-acetoxymethyl-2-carboxy-7-[(1,3-dithiol-2-on-4-yl)acetamido]-8-oxo-5-thia-1-aza-bicyclo[4.2.0]oct-2-ene (7.6 g.).

$[\alpha]_D^{20} = + 66.9° \pm 1.5°$ (c.=1, dimethylformamide)

| Calculated | % | C 41.85 | H 3.28 | N 6.51 | O 26.02 | S 22.34 |
|---|---|---|---|---|---|---|
| Found | % | 42.1 | 3.5 | 6.3 | 26.1 | 21.9 |

3-Acetoxymethyl-7-amino-2-tertio butoxycarbonyl-8-oxo-5-thia-1-aza-bicyclo[4.2.0]oct-2-ene can be prepared according to R. J. Stedman, J. Med. Chem. 9, 444 (1966).

(1,3-Dithiol-2-on-4-yl)-acetic acid can be prepared by adding 80% (volume/volume) sulphuric acid (500 cc.), with cooling in an ice bath, to ethyl 4-ethoxythiocarbonylthio-3-oxo-butyrate (161 g.). The temperature rises to 45° C., and the mixture is then heated at 80° C., for 30 minutes. The deep brown solution obtained is cooled and poured into distilled water (2.5 liters). The mixture is heated under reflux for 1 hour. It is then cooled and extracted 4 times with ethyl acetate (500 cc.), and the organic extracts are washed with distilled water (500 cc.) and extracted 3 times with a saturated solution of sodium bicarbonate (500 cc.). The basic fractions are combined and washed with ethyl acetate (500 cc.) and the aqueous phase is acidified to pH 1 with 4 N hydrochloric acid. It is extracted with ethyl acetate (3 times 500 cc.) and the organic phase is washed with distilled water (500 cc.), dried over magnesium sulphate and treated with decolourising charcoal, and the filtrate is concentrated to dryness under reduced pressure (20 mm.Hg). An ochre solid (96 g.) is obtained, which is recrystallised from a mixture (150 cc.) of ethyl acetate and cyclohexane (50—50 by volume) to give 68.7 g. of the desired product as white crystals m.p. 99° C.

Ethyl 4-ethoxythiocarbonylthio-3-oxo-butyrate can be prepared by cooling a suspension of potassium ethylxanthate (160 g.) in 2 liters of ethanol in an ice bath. A solution of ethyl γ-bromoacetoacetate (209 g.) in ethanol (500 cc.) is added over the course of 1 hour. The reagents are left in contact for 16 hours at a temperature of about 20° C., the suspension obtained is then filtered, the precipitate is washed twice with ethanol (100 cc.) and the filtrate is then concentrated to dryness under reduced pressure (20 mm.Hg). A brown oil (260 g.) is obtained, which is chromatographed on silica gel (2,000 g.). Elution is carried out with a mixture of ethyl acetate and cyclohexane (5–95 by volume) (6 liters) and then with a mixture of ethyl acetate and cyclohexane (10–90 by volume) (10 liters). These eluates are concentrated under reduced pressure to give 161.2 g. of the desired product as an orange oil.

Ethyl γ-bromoacetoacetate can be prepared according to A. Burger and G. E. Ullyot, J. Org. Chem., 12, 346, (1947).

(1,3-Dithiol-2-on-4-yl)-acetic acid can also be prepared by dissolving sodium isopropylxanthate dihydrate (620 g.) in distilled water (1,500 cc.) in a 4 l three-neck flask. Methyl γ-chloroacetoacetate (450 g.) is added to the resulting solution at such a rate that the temperature does not exceed 40° C. The mixture is then stirred for 1 hour, ethyl acetate (1,500 cc.) is added and the whole is stirred for 5 minutes. The organic phase is separated off and the aqueous phase is again extracted with ethyl acetate (500 cc.). The organic fractions are combined, washed with a saturated aqueous solution of sodium chloride (300 cc.), dried over magnesium sulphate (150 g.) and concentrated under reduced pressure (15 mm.Hg). The residue (765 g.) is added to 80% sulphuric acid (1,500 cc.) at such a rate that the temperature of the solution does not rise above 30° C. The mixture is left stirring for 1 hour and is then diluted by adding distilled water (9,300 cc.) and heated under reflux for 2½ hours. The reaction mixture is cooled and extracted three times with ethyl acetate (1,000 cc.). The organic fractions are combined, washed with water (200 cc.) and extracted five times with a saturated sodium bicarbonate solution (700 cc.). The aqueous phases are combined, washed with ethyl acetate (500 cc.) and then brought to pH 1 by adding 4 N hydrochloric acid in the presence of ethyl acetate (2,500 cc.). The organic phase is separated off and the aqueous phase is again extracted with ethyl acetate (500 cc.). The combined organic fractions are washed with a saturated sodium chloride solution (200 cc.), dried over magnesium sulphate (500 g.), filtered in the presence of decolourising charcoal (50 g.) and concentrated under reduced pressure (15 mm.Hg). The residue (386 g.) is recrystallised from a mixture of ethyl acetate and cyclohexane (4:5 by volume) (1,800 cc.) to give 281 g., after drying, of the desired product as cream crystals m.p. 100° C.

EXAMPLE 2

One drop of dimethylformamide is added to a suspension of (1,3-dithiol-2-on-4-yl)-acetic acid (35.2 g.) in anhydrous ethyl ether (400 cc.). The mixture is cooled in an ice bath and oxalyl chloride (34 cc.) is then added dropwise. A vigorous evolution of gas is observed and the mixture becomes limpid. The reagents are left in contact for 1½ hours and the mixture is flushed with nitrogen and concentrated to dryness under reduced pressure (20 mm.Hg) at a temperature of about 20° C. The yellow, partially crystalline, residue is dissolved in acetone (300 cc.) and added to a solution, which is kept at 2° C., of 7-amino-cephalosporanic acid (54.4 g.) and sodium bicarbonate (37 g.) in distilled water (800 cc.) and acetone (600 cc.) over the course of one hour. The reagents are left in contact for 18 hours at a temperature of between 0°, and 10° C., and the acetone is then driven off under reduced pressure (20 mm.Hg). The aqueous solution is washed with ethyl acetate (500 cc.) and then acidified to pH 2 in the presence of ethyl acetate (500 cc.) by adding 4 N hydrochloric acid. The organic and aqueous phases are filtered through "Supercel", the organic phase is separated off, the aqueous phase is extracted twice with ethyl acetate (250 cc.), and the organic fractions are combined and washed twice with distilled water (250 cc.). They are dried over magnesium sulphate and then evaporated to dryness under reduced pressure (20 mm.Hg). The residue is recrystallised from methanol (180 cc.) to give 3-acetoxymethyl-2-carboxy-7-[(1,3- dithiol-2-on-4-yl)-acetamido]-8-oxo-5-thia-1-azabicyclo[4.2.0]oct-2-ene (32.7 g.).

$[\alpha]_D^{20} = +69.8° \pm 1.3°$ (c = 1, dimethylformamide)

EXAMPLE 3

A solution of (1,3-dithiol-2-on-4-yl)-acetyl chloride (13.2 g.) in chloroform (110 cc.) is added to a solution of 7-amino-3-methyl-8-oxo-2-(2,2,2-trichloroethoxycarbonyl)-5-thia-1-aza-bicyclo[4.2.0]oct-2-ene (23 g.) and triethylamine (9.5 cc.) in chloroform (300 cc.), maintained at −10° C., over the course of 1 hour. The reagents are left in contact for 24 hours at a temperature of between 0° and 10° C., and the chloroform is then driven off under reduced pressure (20 mm.Hg). The residue is taken up in ethyl acetate (one liter) and the solution is washed first with an 0.1 N hydrochloric acid solution (250 cc.), then with a saturated aqueous sodium bicarbonate solution (250 cc.) and finally twice with water (250 cc.). The organic phase is dried over magnesium sulphate, treated with decolourising charcoal and filtered. The filtrate is concentrated under reduced pressure (20 mm.Hg) to a volume of 100 cc. and then added to isopropyl ether (one liter). The product, 3-methyl-8-oxo-7-[(1,3-dithiol-2-on-4-yl)-acetamido]-2-(2,2,2-trichloroethoxycarbonyl)-5-thia-1-aza-bicyclo[4.2.0]oct-2-ene (27 g.) precipitates and is filtered off. This product (17 g.) is dissolved in dimethylformamide (120 cc.) and acetic acid (35 cc.). The mixture is cooled in an ice bath, zinc powder (20.8 g.) is added and the mixture is stirred for 3½ hours. The reaction mixture is then filtered; ethyl acetate (400 cc.) is added to the filtrate and the mixture is washed twice with water (a total of 400 cc.). The organic phase is extracted three times with a saturated sodium bicarbonate solution (200 cc.). The alkaline solution is acidified to pH 2.5 by adding 4 N hydrochloric acid in the presence of ethyl acetate (400 cc.). After decanting the organic phase, the aqueous phase is extracted twice with ethyl acetate (a total of 200 cc.); the organic extracts are combined, washed twice with water (a total of 200 cc.), dried over magnesium sulphate, treated with decolourising charcoal and filtered. The filtrate is concentrated to dryness under reduced pressure (20 mm.Hg). The residue obtained is recrystallised from a mixture of acetone and petroleum ether (100 cc.) to give 2-carboxy-3-methyl-8-oxo-7-[(1,3-dithiol-2-on-4-yl)-acetamido]-5-thia-1-aza-bicyclo[4.2.0]-oct-2-ene (3.5 g.).

$[\alpha]_D^{20} = +131° \pm 2°$ (c = 1, dimethylformamide)

| Calculated % = | C 41.92 | H 3.25 | N 7.52 | O 21.43 | S 25.83 |
|---|---|---|---|---|---|
| Found | 42.5 | 3.5 | 7.1 | 22.2 | 24.7 |

(1,3-Dithiol-2-on-4-yl)-acetyl chloride can be obtained by adding oxalyl chloride (36 g.) to a solution of (1,3-dithiol-2-on-4-yl)-acetic acid (35.2 g.) in anhydrous ethyl ether (500 cc.). A slight evolution of hydrochloric acid gas occurs and dimethylformamide (three drops) is then added. The evolution of gas becomes very rapid and lasts for 30 minutes. A further three drops of dimethylformamide are added and the mixture is stirred for 30 minutes. A yellow oil sticks to the bottom of the flask. The ether phase is decanted and concentrated to dryness under reduced pressure (300 mm.Hg followed by 15 mm.Hg). The crystalline residue is washed three times with petroleum ether (boiling point = 40°–65° C.) (300 cc.) and the crystals are dried under reduced pressure (15 mm.Hg). A grey solid (34 g.) is obtained and is recrystallised from a mixture of cyclohexane and toluene (40:6 by volume) (460 cc.). to give the desired product (29 g.) as white crystals m.p. 65° C.

7-Amino-3-methyl-8-oxo-2-(2,2,2-trichloroethoxycarbonyl)-5-thia-1-aza-bicyclo[4.2.0]oct-2-ene can be prepared according to R. R. CHAUVETTE and colleagues, J. Org. Chem., 36, 1259 (1971).

EXAMPLE 4

Sodium azide (0.871 g.) is added to a solution of 3-acetoxymethyl-2-carboxy-8-oxo-7-[(1,3-dithiol-2-on-4-yl)acetamido]-5-thia-1-aza-bicyclo[4.2.0]oct-2-ene (3 g.) in water (60 cc.) and sodium bicarbonate (0.588 g.), and the mixture is heated to 50° C. for 16 hours. It is allowed to cool and sodium bicarbonate (0.4 g.) is added. The mixture is extracted twice with ethyl acetate (40 cc.). The aqueous phase is treated with decolourising charcoal and brought to pH 2 by adding 6 N hydrochloric acid. A product precipitates, and is extracted with ethyl acetate (240 cc.). The organic extracts are dried over sodium sulphate and then concentrated to dryness under reduced pressure (20 mm.Hg). A residue (1.9 g.) is obtained, which is recrystallised from acetonitrile (18 cc.) to give 3-azidomethyl-2-carboxy-8-oxo-7-[(1,3-dithiol-2-on-4-yl)-acetamido]-5-thia-1-aza-bicyclo[4.2.0]oct-2-ene (1.29 g.), m.p. 160° C., after a further recrystallisation from acetonitrile.

$[\alpha]_D^{20} = +71°, 4 \pm 1.3°$ (c = 1, dimethylformamide)

EXAMPLE 5

3-Acetoxymethyl-2-carboxy-8-oxo-7-[(1,3-dithiol-2-on-4-yl)-acetamido]-5-thia-1-aza-bicyclo[4.2.0]oct-2-ene (7 g.) is dissolved in distilled water (100 cc.) and sodium bicarbonate (1.46 g.). A solution of 2-thioxo-1,3,4-thiadiazoline (1.92 g.) in distilled water (60 cc.) and sodium bicarbonate (1.46 g.) is added and the resulting solution is heated to 60° C., for 6 hours. Afer cooling, it is acidified to pH 5.5 by adding 4 N hydrochloric acid and is then extracted twice with ethyl acetate (100 cc.). The organic extracts are discarded. The acidification is continued, in the presence of ethyl acetate (250 cc.) until the pH is 2. After decanting the organic phase, the aqueous phase is extracted twice with ethyl acetate (a total of 200 cc.). The combined organic extracts are washed twice with water (200 cc.), dried over magnesium sulphate, treated with decolourising charcoal and then concentrated to dryness under reduced pressure (20 mm.Hg). 2-Carboxy-8-oxo-7-[(1,3-dithiol-2-on-4-yl)-acetamido]-3-[(1,3,4-thiadiazol-2-yl)-thiomethyl]-5-thia-1-aza-bicyclo[4.2.-0]oct-2-ene, (4.5 g.), solvated with about 10% of ethyl acetate, is thus obtained. The sodium salt of this product is obtained by dissolving the corresponding acid in an 0.1 N aqueous sodium bicarbonate solution and lyophilising the mixture.

$[\alpha]_D^{20} = +26° \pm 1°$ (c = 1, dimethylformamide)

| Calculated % | C 35.29 | H 2.17 | N 10.98 | O 15.66 | S 31.40 |
|---|---|---|---|---|---|
| Found | 35.3 | 2.5 | 10.2 | 17.6 | 30.6 |

EXAMPLE 6

3-Acetoxymethyl-2-carboxy-8-oxo-7-[(1,3-dithiol-2-on-4-yl)-acetamido]-5-thia-1-aza-bicyclo[4.2.0]oct-2-ene (8.8 g.) is dissolved in distilled water (100 cc.) and sodium bicarbonate (1.72 g.). A solution of 2-methyl-5-thioxo-1,3,4-thiadiazoline (2.7 g.) in distilled water (100 cc.) and sodium bicarbonate (1.72 g.) is added and the resulting solution is heated to 60° C. for 6 hours. After cooling, it is acidified to pH = 5.5 by adding 4 N hydrochloric acid and the extracted twice with ethyl acetate (100 cc.). The organic extracts are discarded. The acidification is continued in the presence of ethyl acetate (200 cc.) until the pH is 2. After decanting the organic phase, the aqueous phase is extracted twice with ethyl acetate (a total of 200 cc.). The organic extracts are washed twice with water (200 cc.), dried over magnesium sulphate, treated with decolourising charcoal and then filtered and concentrated under reduced pressure (20 mm.Hg) to a final volume of 25 cc. The solid compound formed is removed by filtration and washed twice with isopropyl ether (25 cc.). After drying under reduced pressure (0.5 mm.Hg), 2-carboxy-3-[(5-methyl-1,3,4-thiadiazol-2-yl)-thiomethyl]-8-oxo-7-[(1,3-dithiol-2-on-4-yl)-acetamido]-5-thia-1-azabicyclo[4.2.0]oct-2-ene (5.5 g.) is obtained.

$[\alpha]_D^{20} = -89.9° \pm 1.5°$ (c = 1, dimethylformamide).

| | C | H | N | O | S |
|---|---|---|---|---|---|
| Calculated % | 38.24 | 2.80 | 11.15 | 15.91 | 31.90 |
| Found | 38.7 | 2.8 | 11.0 | 17.6 | 31.5 |

EXAMPLE 7

3-Acetoxymethyl-2-carboxy-8-oxo-7-[(1,3-dithiol-2-on-4-yl)-acetamido]-5-thia-1-aza-bicyclo[4.2.0]oct-2-ene (7 g.) is dissolved in distilled water (100 cc.) and sodium bicarbonate (1.46 g.). A solution of 5-ethyl-2-thioxo-1,3,4-thiadiazoline (2.63 g.) in distilled water (60 cc.) and sodium bicarbonate (1.46 g.) is added and the resulting solution is heated to 60° C. for 6 hours. After cooling, it is acidified to pH 5.5 by adding 4 N hydrochloric acid and is then extracted twice with ethyl acetate (100 cc.). The organic extracts are discarded. The acidification is continued in the presence of ethyl acetate (300 cc.) until the pH is 2. After decanting the organic phase, the aqueous phase is extracted twice with ethyl acetate (a total of 200 cc.). The combined organic extracts are washed twice with water (200 cc.), dried over magnesium sulphate, treated with decolourising charcoal and then filtered and concentrated to dryness under reduced pressure (20 mm.Hg). The residue obtained is recrystallised from methanol (100 cc.) to give 2-carboxy-3-[(5-ethyl-1,3,4-thiadiazol-2-yl)-thiomethyl]-8-oxo-7-[(1,3-dithiol-2-on-4-yl)-acetamido]-5-thia-1-aza-bicyclo[4.2.0]oct-2-ene (2 g.) m.p. 155° C.

$[\alpha]_D^{20} = -89° \pm 1.5°$ (c = 1, dimethylformamide)

| | C | H | N | O | S |
|---|---|---|---|---|---|
| Calculated % | 39.52 | 3.12 | 10.84 | 15.49 | 31.03 |
| Found | 39.5 | 3.5 | 10.4 | 16.6 | 30.2 |

EXAMPLE 8

5-Methoxy-2-thioxo-1,3,4-thiadiazoline (4.43 g.) and sodium bicarbonate (2.27 g.) in water (20 cc.) are added to the sodium salt of 3-acetoxymethyl-2-carboxy-8-oxo-7-[(1,3-dithiol-2-on-4-yl)-acetamido]-5-thia-1-aza-bicyclo[4.2.0]oct-2-ene (12.2 g.) in a buffer (100 cc.) of pH 6.5. The mixture is heated under a nitrogen atmosphere to 50° C., for 5 hours. It is allowed to cool and treated with decolourising charcoal. Ethyl acetate (100 cc.) is added and the mixture is brought to pH 2.5 by adding 5 N hydrochloric acid while stirring. The organic phase is separated off and the aqueous phase is again extracted with ethyl acetate (160 cc.). The combined organic extracts are dried over sodium sulphate, treated with decolourising charcoal and then concentrated to dryness under reduced pressure (20 mm.Hg). A residue (11.5 g.) is obtained, and is triturated with acetonitrile (8 cc.) and isopropyl ether (8 cc.). A solid (2.4 g.) is filtered off and recrystallised from acetonitrile (375 cc.) and isopropyl ether (400 cc.) to give 2-carboxy-3-[(5-methoxy-1,3,4-thiadiazol-2-yl)-thiomethyl]-8-oxo-7-[(1,3-dithiol-2-on-4-yl)-acetamido]-5-thia-1-aza-bicyclo[4.2.0]oct-2-ene (1.52 g.) m.p. 208° C.

$[\alpha]_D^{20} = -96.0° \pm 1.5°$ (c = 1, dimethylformamide).

EXAMPLE 9

5-Methylthio-2-thioxo-1,3,4-thiadiazoline (2.21 g.) and sodium bicarbonate (1.13 g.) in water (10 cc.) are added to the sodium salt of 3-acetoxymethyl-2-carboxy-8-oxo-7-[(1,3-dithiol-2-on-4-yl)-acetamido]-5-thia-1-aza-bicyclo[4.2.0]oct-2-ene (6.1 g.) in a buffer (50 cc.) of pH 6.5. The mixture is heated under a nitrogen atmosphere to 50° C., for 16 hours, allowed to cool, diluted with water (50 cc.) and then extracted with ethyl acetate (200 cc.). The organic extracts are discarded. The aqueous phase is treated with decolourising charcoal and brought to pH 2 by addition of 6 N hydrochloric acid in the presence of ethyl acetate (80 cc.). The organic phase is separated off and the aqueous phase is again extracted with ethyl acetate (250 cc.). The combined organic extracts are dried over sodium sulphate, treated with decolourising charcoal and concentrated to dryness under reduced pressure (20 mm.Hg). A residue (3.7 g.) is obtained, which is triturated in acetonitrile (15 cc.). A solid is filtered off and is washed with acetonitrile (6 cc.) and isopropyl ether (20 cc.). A product (2.15 g) melting at 156°–159° C. is obtained, which is recrystallised from acetonitrile (160 cc.) and isopropyl ether (240 cc.). 2-Carboxy-3-[(5-methylthio-1,3,4-thiadiazol-2-yl)-thiomethyl]-8-oxo-7-[(1,3-dithiol-2-on-4-yl)acetamido]-5-thia-1-aza-bicyclo[4.2.0]oct-2-ene (1.2 g.) m.p. 160° C., is thus obtained.

$[\alpha]_D^{20} = -112° \pm 2°$ (c = 1, dimethylformamide)

EXAMPLE 10

5-Mesyl-2-thioxo-1,3,4-thiadiazoline (1.31 g.), followed by 3-acetoxymethyl-2-carboxy-8-oxo-7-[(1,3-dithiol-2-on-4-yl)-acetamido]-5-thia-1-aza-bicyclo[4.2.0]oct-2-ene (2.36 g.), followed by potassium thiocyanate (10.7 g.) is added to a solution of sodium bicarbonate (1.01 g.) in water (10 cc.). The mixture is heated to 60° C., for 8 hours. It is allowed to cool, water (50 cc.) is added and the pH is adjusted to 7 by adding sodium bicarbonate. The mixture is extracted with ethyl acetate (50 cc.) and the organic extract is discarded. The aqueous phase is treated with decolourising charcoal, ethyl acetate (40 cc.) is added and the mixture is acidified to pH 2 by adding 4 hydrochloric acid. The organic phase is separated off and the aqueous phase is extracted with ethyl acetate (120 cc.). The combined organic extracts are washed with water (120 cc.), then dried over sodium sulphate and concentrated to dryness under reduced pressure (20 mm.Hg.). A residue (1.9 g.) is obtained, which is triturated with ethyl ether (25 cc.). A solid is filtered off and washed with ethyl ether (40 cc.). A pulverulent powder (1.78 g.) is obtained.

Some of this product (1.36 g.) is dissolved in water (6 cc.) and sodium bicarbonate (0.2 g.). Ethanol (40 cc.) is added and the mixture is heated to 40° C. On cooling to 4° C., a product crystallises and is filtered off. The sodium salt of 2-carboxyl-3-[(5-mesyl-1,3,4-thiadiazol-2-yl)-thio-methyl]-8-oxo-7-[(1,3-dithiol-2-on-4-yl)-acetamido]-5-thia-1-aza-bicyclo[4.2.0]oct-2-ene (0.58 g.) is thus obtained.

Nuclear magnetic resonance spectrum (D$_2$O): 6.85 (singlet, 1H) —H of the dithiol ring; 5.65 and 5.1 (doublets, 1H), —H of the β-lactam; 4.4 (AB, 2H) —CH$_2$S—; 3.70 (massive, 4H) —CH$_2$CO— and methylenic protons of the dihydrothiazine ring; 3.55 (singlet, 3H), —CH$_3$.

5-Mesyl-2-thioxo-1,3,4-thiadiazoline can be obtained by adding phosphorus pentasulphite (12 g.) to 5-mesyl-2-oxo-1,3,4-thiadiazoline (3.6 g.) in xylene (150 cc.) and heating the mixture under reflux in a nitrogen atmosphere for 26 hours. It is allowed to cool and the organic phase is decanted and extracted with a saturated aqueous sodium bicarbonate solution (500 cc.). The combined aqueous extracts are washed with ethyl ether (80 cc.) and acidified to pH 2 by adding concentrated sulphuric acid. An oil separates out, which is extracted with ethyl acetate (500 cc.). The combined organic extracts are washed with water (100 cc.) dried over sodium sulphate and concentrated to dryness under reduced pressure (20 mm.Hg). A residue (2.2 g.) is obtained, which is recrystallised from a mixture of ethyl ether (3 cc.) and isopropyl ether (3 cc.) to give 0.62 g. of the desired product, m.p. 148° C.

5-Mesyl-2-oxo-1,3,4-thiadiazoline can be obtained by adding hydrogen peroxide (110 volumes) (27.6 cc.) to a solution of 5-methylthio-2-oxo-1,3,4-thiadiazoline (17.7 g.) in acetic acid (180 cc.). The mixture is allowed to react overnight at ordinary temperature. It is then concentrated to about one-quarter of its initial volume, under reduced pressure (20 mm.Hg). A product crystallises and is filtered off; (14.3 g.), m.p. 159° C., which is recrystallised from ethanol (32 cc.) to give the desired product (11.6 g.) m.p. 162° C.

EXAMPLE 11

5-Amino-2-thioxo-1,3,4-thiadiazoline (4.8 g.), 3-acetoxymethyl-2-carboxy-8-oxo-7-[(1,3-dithiol-2-on-4-yl)acetamido]-5-thia-1-aza-bicyclo[4.2.0]oct-2-ene (12.9 g.) and then potassium thiocyanate (58 g.) are added to a solution of sodium bicarbonate (5.52 g.) in water (50 cc.). The reaction mixture is heated to 60° C., for 7 hours. It is allowed to cool and diluted with water (60 cc.) and the mixture obtained is washed with ethyl acetate (180 cc.). Ethyl acetate (100 cc.) is added and the pH is brought to 3 by adding 4 N hydrochloric acid, whilst stirring. A product precipitates, which is filtered off. The solid obtained, weighing 12.8 g., is extracted six times with methanol (100 cc.). On concentrating the methanol filtrates to dryness under reduced pressure (20 mm.Hg), a residue (4.2 g.) is obtained, which is purified by recrystallisation from a mixture of ethanol (85 cc.) and water (15 cc.) to give 3-[(5-amino-1,3,4-thiadiazol-2-yl)-thiomethyl]2-carboxyl-8-oxo-7-[(1,3-dithiol-2-on-4-yl)-acetamido]-5-thia-1-aza-bicyclo[4.2.0]oct-2-ene (2 g.).

$[\alpha]_D^{20} = -103.5° \pm 1.5°$ (c = 1, dimethylformamide).

| | | | | | |
|---|---|---|---|---|---|
| Calculated % | C 35.78 | H 2.60 | N 13.91 | O 15.88 | S 31.83 |
| Found | 35.53 | 2.99 | 13.19 | 16.05 | 31.13 |

EXAMPLE 12

A mixture of 3-acetoxymethyl-2-carboxy-8-oxo-7-[(1,3-dithiol-2-on-4-yl)-acetamido]-5-thia-1-aza-bicyclo-[4.2.0]-oct-2-ene (12.9 g.) in water (50 cc.), sodium bicarbonate (5.52 g.) and 5-acetylamino-2-thioxo-1,3,4-thiadiazoline (6.3 g.) and potassium thiocyanate (58 g.) is heated to 60° C. for 10 hours. The mixture is allowed to cool and diluted with 1 liter of water. A slight amount of insoluble matter is filtered off on "Supercel" and the filtrate is washed with ethyl acetate (250 cc.), which is discarded. It is brought to pH 2 by adding 4 N hydrochloric acid in the presence of ethyl acetate (250 cc.). A solid (6.3 g.) is filtered off and taken up in boiling methanol (200 cc.). An insoluble material is filtered off and the filtrate is concentrated to dryness under reduced pressure (20 mm.Hg). The solid residue obtained is washed with methanol (5 cc.) to give 3-[(5-acetylamino-1,3,4-thiadiazol-2-yl)-thiomethyl]-2-carboxyl-8-oxo-7-[(1,3-dithiol-2-on-4-yl)-acetamido]-5-thia-1-aza-bicyclo[4.2.0]oct-2-ene (2.9 g.).

$[\alpha]_D^{20} = -108.5° \pm 2°$ (c = 1, dimethylformamide).

| | | | | | |
|---|---|---|---|---|---|
| Calculated % | C 37.42 | H 2.77 | N 12.84 | O 17.59 | S 29.38 |
| Found | 37.00 | 2.89 | 12.74 | 18.51 | 28.84 |

EXAMPLE 13

5-Thioxo-1,2,3,4-tetrazoline (2.24 g.), the sodium salt of 3-acetoxymethyl-2-carboxy-8-oxo-7-[(1,3-dithiol-2-on-4-yl)-acetamido]-5-thia-1-aza-bicyclo[4.2.0]-oct-2-ene (8.4 g.) and then potassium thiocyanate (36 g.) are added to a solution of sodium bicarbonate (1.87 g.) in water (32 cc.). The reaction mixture is heated to 60° C., for 4 hours 30 minutes. It is allowed to cool, diluted to a volume of 300 cc. by adding water and brought to pH 2 by adding 4 N hydrochloric acid. A product precipitates, which is filtered off and washed with water (150 cc.). A first batch of solid (5.7 g.) is thus obtained. The filtrate is extracted with ethyl acetate (400 cc.) and the organic extract is washed with water (100 cc.), dried over sodium sulphate and concentrated to dryness under reduced pressure (2 mm.Hg). The residue is dissolved in tetrahydrofuran (50 cc.) and the solution obtained is added dropwise to isopropyl ether (1 liter). A product precipitates, and is filtered off. A second batch of solid (2 g.) is thus obtained.

The two batches of solid are combined and dissolved in acetone (100 cc.), silica (15 g.) is added to the solution and finally the acetone is driven off under reduced pressure (20 mm.Hg). The powder obtained is charged onto a silica column (30 g.). It is eluted with ethyl acetate (1.3 liters) and the eluate is concentrated to dryness under reduced pressure (2 mm.Hg). The residue obtained (6.2 g.) is dissolved in tetrahydrofuran (50 cc.) and the solution obtained is added dropwise to isopropyl ether (750 cc.), to precipitate 2-carboxy-8-oxo-7-[(1,3-dithiol-2-on-4-yl)-acetamido]-3-[(1,2,3,4-tetrazol-5-yl)-thiomethyl]5-thia-1-aza-bicyclo[4.2.0]-oct-2-ene (4.5 g.) which is filtered off.

$[\alpha]_D^{20} = -46° \pm 1°$ (c = 1, dimethylformamide).

| Calculated % | C 35.59 | H 2.56 | N 17.78 | O 16.93 | S 27.14 |
|---|---|---|---|---|---|
| Found | 35.78 | 2.64 | 16.72 | 15.59 | 27.01 |

EXAMPLE 14

A mixture of the sodium salt of 3-acetoxymethyl-2-carboxy-7-[(1,3-dithiol-2-on-4-yl)-acetamido]-5-thia-8-oxo-1-aza-bicyclo[4.2.0]-oct-2-ene (78 g.) dissolved in water (250 cc.), 1-methyl-5-thioxo-1,2,3,4-tetrazoline (24.1 g.), sodium bicarbonate (17.5 g.) and sodium thiocyanate (336 g,) is heated to 50° C. for 5 hours. The mixture is allowed to cool, diluted with water (1 liter) and brought to pH 2 by adding 4 N hydrochloric acid. A product precipitates, which is filtered off and stirred with water (2 liter). The product is again filtered off and washed with water (1 liter). A pulverulent solid (39.9 g.) is obtained. The combined filtrates are extracted three times with ethyl acetate (500 cc.) and the organic phase is washed with water (1 liter) and then extracted with a saturated aqueous solution of sodium bicarbonate (400 cc.). The ethyl acetate dissolved in the aqueous phase is driven off at 40° C., in vacuo (20 mm.Hg), and the aqueous phase is brought to pH 2 by adding 4 N hydrochloric acid. A product precipitates, which is filtered off and washed with water (500 cc.). A second batch of pulverulent solid (11.5 g.) is thus obtained.

The two batches of solid are combined and dissolved in acetone (400 cc.); silica (100 g.) is added and the acetone is then driven off under reduced pressure (20 mm.Hg). The powder obtained is charged onto a column of silica (154 g.) and eluted with ethyl acetate (8 liters). The eluate is concentrated to dryness under reduced pressure. A solid residue (45.6 g.) is obtained, which is dissolved in a solution of sodium bicarbonate (8.13 g.) in water (137 cc.). Ethanol (318 cc.) is added, and the sodium salt of 3-[(1-methyl-1,2,3,4-tetrazol-5-yl)-thiomethyl]-2-carboxyl-7-[(1,3-dithiol-2-on-4-yl)-acetamido]-8-oxo-5-thia-1-aza-bicyclo[4.2.0]oct-2-ene (22.1 g.) crystallises which is filtered off.

$[\alpha]_D^{20} = +37.2° \pm 1°$ (c = 1, water).

| Calculated % | C 34.22 | H 2.87 | N 15.96 | Na 4.36 | O 18.23 | S 24.36 |
|---|---|---|---|---|---|---|
| Found | 34.8 | 3.0 | 15.8 | 4.25 | | 23.65 |

EXAMPLE 15

The sodium salt of 3-acetoxymethyl-2-carboxy-8-oxo-7-[(1,3-dithiol-2-on-4-yl)-acetamido]-5-thia-1-aza-bicyclo[4.2.0]oct-2-ene (12.2 g.) is dissolved in a buffer solution (350 cc.) of pH 6.2, consisting of monopotassium phosphate (47.1 g.), N sodium hydroxide solution (80.9 cc.) and water. Sodium bicarbonate (2.6 g.) is added to this solution, followed by 1-ethyl-5-thioxo-1,2,3,4-tetrazoline (4 g.), and the mixture is heated to 60° C for 6 hours, whilst stirring. After cooling, the reaction mixture is washed twice with ethyl acetate (150 cc.). It is then acidified to pH 2 by adding 4 N hydrochloric acid in the presence of ethyl acetate (350 cc.). After decanting the organic phase, the aqueous phase is extracted twice with ethyl acetate (a total of 150 cc.). The organic extracts are combined, washed twice with water (a total of 300 cc.), dried over sodium sulphate, treated with decolourizing charcoal, filtered and then concentrated to dryness under reduced pressure (20 mm Hg). A residue (11 g.) is obtained, which is dissolved in ethyl acetate (200 cc.). A 0.6 N solution (30 cc.) of sodium 2-ethylhexanoate in butanol is added to the above solution. A product precipitates. The mixture is stirred for 1 hour and the solid is filtered off, washed with ethyl acetate (100 cc.) and then with isopropyl ether (100 cc.) and dried under reduced pressure (0.1 mm Hg) to give the sodium salt of 2-carboxy-3-[(1-ethyl-1,2,3,4-tetrazol-5-yl)-thiomethyl]-8-oxo-7-[(1,3-dithiol-2-on-4-yl)-acetamido]-5-thia-1-aza-bicyclo[4.2.0]oct-2-ene (5.2 g.).

$[\alpha]_D^{20} = +34.7° \pm 1°$ (c = 1, water).

| Calculated % | C 36.78 | H 2.89 | Na 4.40 | O 15.31 | S 24.54 |
|---|---|---|---|---|---|
| Found | 36.7 | 3.0 | 5.3 | 15.0 | 24.7 |

EXAMPLE 16

The sodium salt of 3-acetoxymethyl-2-carboxy-8-oxo-7-[(1,3-dithiol-2-on-4-yl)-acetamido]-5-thia-1-aza-bicyclo[4.2.0]oct-2-ene (12 g.) is dissolved in water (22 cc.). Potassium thiocyanate (29 g.), sodium bicarbonate (2.45 g.) and 1-tert-butyl-5-thioxo-1,2,3,4-tetrazoline (4.6 g.) are added to this solution and the mixture is heated to 60° C for 6 hours. After cooling, the reaction mixture is diluted with water (150 cc.) and washed with ethyl acetate (200 cc.) after having been acidified to pH 5.5 by adding 4 N hydrochloric acid. The mixture is then acidified to pH 1.5 by adding 4 N hydrochloric acid in the presence of ethyl acetate (350 cc.). After decanting the organic phase, the aqueous phase is extracted twice with ethyl acetate (a total of 150 cc.). The organic extracts are combined, washed twice with water (a total of 300 cc.), dried over sodium sulphate, treated with decolourising charcoal, filtered and then concentrated to dryness under reduced pressure (20 mm Hg). The residue obtained is dissolved in tetrahydrofuran (60 cc.) and this solution is then poured into isopropyl ether (600 cc.). A product precipitates, which is isolated by filtration and dried under reduced pressure (0.1 mm Hg) to give 2-carboxy-8-oxo-7-[(1,3-dithiol-2-on-4-yl)-acetamido]-3-[(1-tert-butyl-1,2,3,4-tetrazol-5-yl)-thiomethyl]-5-thia-1-aza-bicyclo[4.2.0]oct-2-ene (4.5 g.).

$[\alpha]_D^{20} = -64.2° \pm 1.2°$ (c = 1, dimethylformamide)

| Calculated % | C 40.90 | H 3.81 | N 15.90 | O 15.13 | S 24.26 |
|---|---|---|---|---|---|
| Found | 41.8 | 3.7 | 15.2 | 15.6 | 23.9 |

EXAMPLE 17

A mixture of the sodium salt of 3-acetoxymethyl-2-carboxy-8-oxo-7-[(1,3-dithiol-2-on-4-yl)-acetamido]-5-thia-1-aza-bicyclo[4.2.0]oct-2-ene (14.2 g.) dissolved in water (55 cc.), 1-(2-hydroxyethyl)-5-thioxo-1,2,3,4-tetrazoline (5.5 g.), sodium bicarbonate (3.16 g.) and potassium thiocyanate (61 g.) is heated to 60° C for 4 hours and 30 minutes. The mixture is allowed to cool and is diluted with water (250 cc.) and acidified to pH 2 by adding 4 N hydrochloric acid. It is then extracted with ethyl acetate (2 liters); the organic extracts are washed with water (200 cc.), dried over sodium sulphate and concentrated to dryness under reduced pressure (20 mm Hg). The residue is dissolved in tetrahydrofuran (100 cc.) and the solution obtained is added dropwise to isopropyl ether (2 liters). A product precipitates, which is filtered off. The pulverulent solid obtained (12 g.) is dissolved in acetone (100 cc.); silica (10 g.) is added to this solution and the acetone is driven off under reduced pressure (20 mm Hg). The powder obtained is charged onto a column of silica (15 g.). It is eluted with ethyl acetate (500 cc.) and the eluate is concentrated to dryness under reduced pressure (20 mm Hg). A residue (4.1 g.) is obtained, which is dissolved in tetrahydrofuran (50 cc.). This solution is added dropwise to isopropyl ether (750 cc.) to precipitate 2-carboxy-3-{[1-(2-hydroxyethyl)-1,2,3,4-tetrazol-5-yl]-thiomethyl}-8-oxo-7-[(1,3-dithiol-2-on-4-yl)-acetamido]-5-thia-1-aza-bicyclo[4.2.0]oct-2-ene (3.4 g.) which is filtered off.

$[\alpha]_D^{20} = -72° \pm 1°$ (c = 1, dimethylformamide).

| | C | H | N | O | S |
|---|---|---|---|---|---|
| Calculated % | 37.20 | 3.12 | 16.27 | 18.58 | 24.83 |
| Found | 36.62 | 3.04 | 15.98 | 17.41 | 25.27 |

1-(2-Hydroxyethyl)-5-thioxo-1,2,3,4-tetrazoline can be prepared by adding 2-(2-isothiocyanatoethoxy)-tetrahydropyrane (55 g.) over the course of 30 minutes to a suspension of sodium azide (28.6 g.) in ethanol (400 cc.) under reflux, whilst maintaining a stream of carbon dioxide through the reaction mixture. The reaction is allowed to take place for 6 hours under reflux and the mixture is then left overnight at about 25° C. The suspended solid is filtered off and the filtrate is concentrated to dryness under reduced pressure (20 mm Hg). The residue is taken up in ethyl ether (200 cc.); a product precipitates and is filtered off. A solid (33.5 g.) is obtained and is dissolved in methanol (800 cc.). The solution obtained is acidified by passing a stream of hydrogen chloride gas through it for 1 hour, whilst stirring. A solid is filtered off and the filtrate is concentrated to dryness under reduced pressure (20 mm Hg). A residue (22.4 g.) is obtained, which is recrystallised from a mixture of acetonitrile and 1,2-dichloroethane(-1—1 by volume) (180 cc.), to give the desired product (9.7 g.) m.p. 139° C.

2-(2-Isothiocyanato-ethoxy)-tetrahydropyrane can be prepared by adding a solution of sodium hydroxyde (27.6 g.) in water (100 cc.) to carbon disulphide (52.5 g.) while keeping the temperature below 10° C. 2-(2-Aminoethoxy)-tetrahydropyrane (99.7 g.) is then added dropwise over the course of 15 minutes and the mixture is heated under reflux for 4 hours. It is then allowed to cool to 40° C and while maintaining this temperature ethyl chloroformate (74.5 g.) is added dropwise and the mixture is allowed to react overnight. It is extracted twice with methylene chloride (200 cc.) and the methylene chloride extracts are combined and washed with water (200 cc.). They are dried over sodium sulphate, treated with decolourising charcoal and concentrated to dryness under reduced pressure (20 mm Hz). An oily residue (123.7 g.) is obtained, which is distilled under reduced pressure to give the desired product (55.7 g.), boiling point$_{0.3}$ = 83°–93° C.

EXAMPLE 18

The sodium salt of 3-acetoxymethyl-2-carboxy-8-oxo-7-[(1,3-dithiol-2-on-4-yl)-acetamido]-5-thia-1-aza-bicyclo[4.2.0]oct-2-ene (10 g.) is dissolved in water (51 cc.). Potassium thiocyanate (60 g.), sodium bicarbonate (2.24 g.) and 1-phenyl-5-thioxo-1,2,3,4-tetrazoline (4.75 g.) are added to this solution and the mixture is heated to 60° C for 8 hours. After cooling, the reaction mixture is diluted with water (250 cc.) and washed with ethyl acetate (200 cc.) after acidification to pH 5.5 by adding 4 N hydrochloric acid. The mixture is then acidified to pH 1.5 by adding 4 N hydrochloric acid in the presence of ethyl acetate (100 cc.). After decanting the organic phase, the aqueous phase is extracted four times with ethyl acetate (a total of 400 cc.). The organic extracts are combined, washed three times with an 0.1 N hydrochloric acid solution (a total of 300 cc.) and then twice with water (a total of 300 cc.), dried over sodium sulphate, treated with decolourising charcoal, filtered and then concentrated to dryness under reduced pressure (20 mm Hg). The residue obtained is dissolved in tetrahydrofuran (50 cc.) and this solution is then added to isopropyl ether (1 liter). A product precipitates, which is isolated by filtration and dried under reduced pressure (0.1 mm Hg). 2-Carboxy-8-oxo-7[(1,3-dithiol-2-on-4-yl)-acetamido]-3-[(1-phenyl-1,2,3,4-tetrazol-5-yl)-thiomethyl]-5-thia-1-aza-bicyclo[4.2.0]oct-2-ene (5.4 g.) is thus obtained. $[\alpha]_D^{20} = -17.4° \pm 0.7°$ (c = 1, dimethylformamide).

| | C | H | N | O | S |
|---|---|---|---|---|---|
| Calculated % | 43.79 | 2.94 | 15.32 | 14.58 | 23.37 |
| Found | 43.9 | 3.3 | 13.9 | 15.8 | 23.3 |

EXAMPLE 19

The sodium salt of 3-acetoxymethyl-2-carboxy-8-oxo-7-[(1,3-dithiol-2-on-4-yl)-acetamido]-5-thia-1-azabicyclo[4.2.0]oct-2-ene (6.1 g.) is dissolved in water (20 cc.). Potassium thiocyanate (26.6 g.), sodium bicarbonate (1.38 g.) and 2-methyl-5-thioxo-1,2,3,4-tetrazoline (1.9 g.) are added to this solution and the mixture is heated to 60° C for 5 hours. After cooling, the reaction mixture is diluted with water (100 cc.), acidified to pH 5.8 by adding 4 N hydrochloric acid and washed with ethyl acetate (50 cc.). The aqueous phase is acidified to pH 1.6 by adding 4 N hydrochloric acid in the presence of ethyl acetate (200 cc.). After decanting the organic phase, the aqueous phase is extracted twice with ethyl acetate (a total of 200 cc.). The organic extracts are combined, washed twice with an 0.1 N hydrochloric acid solution (a total of 140 cc.) and then twice with water (a total of 200 cc.), dried over sodium sulphate, treated with decolourising charcoal, filtered and then concentrated to dryness under reduced pressure (20 mm Hg). The residue obtained is dissolved in tetrahydrofuran (25 cc.) and this solution is then added dropwise to isopropyl ether (300 cc.). A product precipitates which is isolated by filtration and dried under reduced pressure (0.1 mm Hg). 2-Carboxy-3[(2-methyl-1,2,3,4-tetrazol-5-yl)-thiomethyl]-8-oxo-7-[(1,3-dithiol-2-on-4-yl)-acetamido]-5-thia-1-aza-bicyclo[4.2.0]oct-2-ene (5.1 g.) is thus obtained. $[\alpha]_D^{20} = -63.4° + 1.2°$ (c = 1, dimethylformamide).

| Calculated % | C 37.03 | H 2.90 | N 17.27 | O 16.44 | S 26.36 |
|---|---|---|---|---|---|
| Found | 37.6 | 3.4 | 16.5 | 16.4 | 25.9 |

2-Methyl-5-thioxo-1,2,3,4-tetrazoline can be prepared by dissolving 5-benzylthio-2-methyl-tetrazole (6 g.) in chlorobenzene (10 cc.) and adding this solution to a solution of aluminium bromide (11.3 g.) in chlorobenzene (25 cc.) at 0° C. The mixture is stirred for 1 hour at 0° C and then for 24 hours at about 25° C. It is cooled in an ice bath, water (20 cc.) is added and the mixture is extracted twice with ether (100 cc.). The organic extracts are combined and treated twice with a saturated sodium bicarbonate solution (a total of 100 cc.). The ether phase is discarded; the aqueous phase is acidified and extracted twice with ether (100 cc.). The extracts are combined, dried over sodium sulphate, treated with charcoal and filtered. The filtrate is concentrated to dryness under reduced pressure (20 mm Hg) to give the desired product (2.5 g.) as an oil which solidifies.

Nuclear magnetic resonance spectrum (CDCl$_3$) 4.12 (s, 1H) —SH; 4.42 (s, 3H) —CH$_3$.

5-Benzylthio-2-methyl-tetrazole can be prepared by suspending 5-benzylthio-tetrazole (10 g.) in ethyl ether (80 cc.). A solution of diazomethane in ether is added whilst stirring and keeping the temperature below 10° C; the suspended product dissolves. The addition is continued until all has dissolved and a slight yellow colouration persists, and the mixture is then stirred for a further hour. The ether phase is washed successively with water (100 cc.), a saturated sodium bicarbonate solution (20 cc.), water (100 cc.), a 4 N hydrochloric acid solution (20 cc.) and water (100 cc.); it is dried over sodium sulphate and the solvent is evaporated under reduced pressure (0.1 mm Hg). A residue (9.8 g.) is obtained, which is chromatographed on silica (150 g.). Elution is carried out successively with cyclohexane (800 cc.), then with a mixture of ethyl acetate and cyclohexane (1–19 by volume) (400 cc.) and then with a mixture of ethyl acetate and cyclohexane (1–9 by volume) (1,400 cc.); on concentrating this fraction under reduced pressure (20 mm Hg), 5-benzylthio-2-methyl-tetrazole (6.3 g.) is obtained as a colourless oil. On continuing the elution with a mixture of ethyl acetate and cyclohexane (1–1 by volume) (400 cc.) and evaporating the solvent under reduced pressure (20 mm Hg), 5-benzylthio-1-methyl-tetrazole (2.9 g.) is obtained as a colourless oil.

Nuclear magnetic resonance spectra: (CDCl$_3$) (s, 2H) —CH$_2$—; 7.42 (m, 5H) —C$_6$H$_5$.

5-Benzylthio-tetrazole can be prepared according to E. LIEBER, J. Org. Chem., 26, 4472 (1961).

EXAMPLE 20

Sodium bicarbonate (5.55 g.) and 3-thioxo-1,2,4-triazoline (3.63 g.) are added to 3-acetoxymethyl-2-carboxy-8-oxo-7-[(1,3-dithiol-2-on-4-yl)-acetamido]-5-thia-1-aza-bicyclo[4.2.0]oct-2-ene (12.9 g.) in a buffer (250 cc.) of pH 6.4. The mixture is heated to 60° C for 7 hours. It is allowed to cool, sodium bicarbonate (1 g.) is added and the mixture is washed with ethyl acetate (250 cc.), which is discarded. The aqueous solution is treated with decolourising charcoal and is acidified to pH 2 by adding 4 N hydrochloric acid in the presence of ethyl acetate (200 cc.). The organic phase is separated off and the aqueous phase is then extracted with ethyl acetate (750 cc.). The combined organic extracts are dried over sodium sulphate, treated with decolourising charcoal and concentrated to dryness under reduced pressure (20 mm Hg). A residue (5.5 g.) is obtained, which is triturated with acetonitrile (25 cc.). The solid is filtered off and washed with acetonitrile (25 cc.) and isopropyl ether (20 cc.) to give 2-carboxy-8-oxo-7-[(1,3-dithiol-2-on-4-yl)-acetamido]-3-[(1,2,4-triazol-3-yl)-thiomethyl]-5-thia-1-aza-bicyclo[4.2.0]oct-2-ene (2.9 g.), m.p. 227° C (decomposition).

$[\alpha]_D^{20} = -74.9° \pm 1.4°$ (c = 1, dimethylformamide)

| Calculated % | C 38.21 | H 2.78 | N 14.83 | O 16.96 | S 27.20 |
|---|---|---|---|---|---|
| Found | 38.3 | 2.8 | 14.4 | 16.65 | 26.5 |

EXAMPLE 21

3-Acetoxymethyl-2-carboxy-8-oxo-7-[(1,3-dithiol-2-on-4-yl)-acetamido]-5-thia-1-aza-bicyclo[4.2.0]-oct-2-ene (7.7 g.) is dissolved in distilled water (100 cc.) and sodium bicarbonate (1.64 g.),. A solution of 4-methyl-2-thioxo-1,3-thiazoline (2.76 g.) in distilled water (75 cc.) and sodium bicarbonate (1.64 g.) is added and the resulting solution is heated to 60° C for 6 hours. After cooling, it is acidified to pH 5.5 by adding 4 N hydrochloric acid and then extracted with ethyl acetate (100 cc.), which is discarded. The acidification is continued to pH 2 in the presence of ethyl acetate (300 cc.). After decanting the organic phase, the aqueous phase is extracted twice with ethyl acetate (a total of 200 cc.). The organic extracts are washed twice with water (200 cc.), dried over magnesium sulphate, treated with decolourising charcoal and then filtered and concentrated to dryness under reduced pressure (20 mm Hg). The residue obtained is dissolved in methanol (30 cc.) and this solution is then added to isopropyl ether (200 cc.). A product precipitates and is isolated by filtration to give 2-carboxy-3-[(4-methyl-1,3-thiazol-2-yl)-thiomethyl]-8-oxo-7-[(1,3-dithiol-2-on-4-yl)-acetamido]-5-thia-1-aza-bicyclo[4.2.0]oct-2-ene (2 g.).

$[\alpha]_D^{20} = -72° \pm 4°$ (c = 1, dimethylformamide).

| Calculated % | C 40.70 | H 3.01 | N 8.38 | O 15.95 | S 31.96 |
|---|---|---|---|---|---|
| Found | 41.4 | 3.0 | 8.1 | 15.8 | 30.0 |

EXAMPLE 22

The sodium salt of 3-acetoxymethyl-2-carboxy-8-oxo-7-([(1,3-dithiol-2-on-4-yl)-acetamido]-5-thia-1-aza-bicyclo[4.2.0]oct-2-ene (10 g.) and potassium thiocyanate (40 g.) are added to a solution of 3-methyl-5-thioxo-1,2,4-thiadiazoline (3.65 g.) and potassium bicarbonate (2.33 g.) in water (30 cc.). The mixture is heated to 60° C. After 2 hours, a precipitate appears and becomes progressively more copious. The reaction mixture is cooled to 0° C after heating for 5 hours and is filtered and the white precipitate is suspended in distilled water (50 cc.) and ethyl acetate (100 cc.) and acidified to pH 1 by adding 4 N hydrochloric acid. The organic phase is dried over magnesium sulphate, filtered and evaporated. The residue (5.5 g.) is suspended in distilled water (50 cc.) and sodium bicarbonate (0.95 g.) is added thereto. The resulting solution is concentrated to dryness under reduced pressure (15 mm Hg) and the ground residue is stirred with distilled water (25 cc.) at 80° C. The suspension is cooled to 0° C and filtered, and the white solid is dried to give the sodium salt of 2-carboxy-3-[(3-methyl-1,2,4-thiadiazol-5-yl)-thiomethyl]-8-oxo-7-[(1,3-dithiol-2-on-4-yl)-acetamido]-5-thia-1-aza-bicyclo[4.2.0]oct-2-ene (2.1 g.) as a white powder.

$[\alpha]_D^{20} = -25° \pm 1°$ (c = 1, dimethylsulphoxide)

| Calculated % | C 36.63 | H 2.50 | N 10.68 | Na 4.38 | O 15.25 |
|---|---|---|---|---|---|
|  | S 30.56 |  |  |  |  |
| Found | C 36.65 | H 2.5 | N 10.3 | Na 4.2 | S 30.5 |

EXAMPLE 23

(1,2,3-Thiadiazol-4-yl)-thiocarboxylic acid (4.9 g.) is added to a solution of sodium bicarbonate (2.85 g.) in distilled water (50 cc.). The sodium salt of 3-acetoxymethyl-2-carboxy-8-oxo-7-[(1,3-dithiol-2-on-4-yl)-acetamido]-5-thia-1-aza-bicyclo[4,2,0]oct-2-ene (12.6 g.) and potassium thiocyanate (54 g.) are added to the yellow solution obtained and the mixture is heated for 4½ hours to 60° C under a nitrogen atmosphere. The cooled solution is diluted to 250 cc. and acidified to pH 2 by adding 4 N hydrochloric acid. The beige precipitate formed is filtered off, washed twice with water (100 cc.), then suspended in water (100 cc.) and extracted with ethyl acetate (200 cc.). The two phases are filtered through "Supercel", and the organic phase is separated off, dried over sodium sulphate and concentrated under reduced pressure (20 mm Hg). The residue is triturated in ethyl ether (100 cc.) and filtered off. A solid (10 g.) is obtained, which is chromatographed over silica gel (60 g.), elution being carried out with ethyl acetate, in fractions of 50 cc.

After 16 hours, fractions 2 and 3 deposit a crystalline precipitate which is filtered off and then dried. 2-Carboxy-8-oxo-7-[(1,3-dithiol-2-on-4-yl)-acetamido]-3-[(1,2,3-thiadiazol-4-yl)-carbonylthiomethyl]-5-thia-1-aza-bicyclo[4.2.0]oct-2-ene (3.1 g.) is thus obtained.

$[\alpha]_D^{20} = -61.5° \pm 1.5°$ (c = 1, dimethylformamide)

| Calculated % | C 37.20 | H 2.35 | N 10.84 | O 18.58 | S 31.03 |
|---|---|---|---|---|---|
| Found | 37.75 | 2.55 | 10.60 | 18.85 | 30.50 |

EXAMPLE 24

Water (50 cc.) and pyridine (8.3 cc.) are added to 3-acetoxymethyl-2-carboxy-8-oxo-7-[(1,3-dithiol-2-on-4-yl)-acetamido]-5-thia-1-aza-bicyclo[4.2.0]-oct-2-ene (22 g.), sodium bicarbonate (4.35 g.) and potassium thiocyanate (99.5 g.). After stirring, a syrupy homogeneous medium is obtained, the pH of which is adjusted to 6.5 by adding concentrated phosphoric acid. The mixture is heated to 60° C for 5 hours. After cooling, it is diluted with distilled water (350 cc.) and washed three times with chloroform (a total of 300 cc.). The last traces of chloroform are removed from the aqueous phase under reduced pressure (20 mm Hg), and this phase is then treated with decolourising charcoal, filtered over "Supercel" and cooled with an ice-water bath. It is acidified to pH = 2 by adding 4 N hydrochloric acid whilst maintaining the temperature below 5° C. After precipitation, the mixture is stirred for 1 hour whilst continuing to cool it with an ice-water bath, and is then washed twice by decanting, using iced water (one liter). The precipitate is isolated by filtration and washed three times with iced water (a total of 300 cc.). The moist solid obtained is suspended in water (100 cc.) and a 25% solution of Amberlite LA 2 in methyl isobutyl ketone (100 cc.) is added. The mixture is stirred until the solid has completely dissolved and the organic phase is then decanted and discarded. The aqueous phase is extracted twice with a 25% Amberlite LA 2 solution in methylisobutyl ketone (a total of 150 cc.), then with ethyl acetate (100 cc.) and finally 3 times with ethyl ether (a total of 300 cc.). The water is evaporated under reduced pressure (20 mm Hg) at 40° C. An oil is obtained which, when triturated in acetone (150 cc.), gives a white solid which is filtered off. The compound obtained is washed three times with acetone (a total of 150 cc.) and then dried under reduced pressure (0.5 mm Hg) to give 2-carboxylato-8-oxo-7-[(1,3-dithiol-2-on-4-yl)-acetamido]-3-(1-pyridinio-methyl)-5-thia-1-aza-bicyclo[4.2.0]oct-2-ene (11.7 g.).

This product is crystallised by dissolving the product (9 g.) in water (10 cc.), and then adding methanol (10 cc.) dropwise. A solution is obtained, which turns cloudy and then deposits a precipitate. The crystals are filtered off and washed twice with methanol (a total of 10 cc.) and then with isopropyl ether (50 cc.). After drying under reduced pressure (0.5 mm Hg), 2-carboxylato-8-oxo-7-[(1,3-dithiol-2-on-4-yl)-acetamido]-3-(1-pyridinio-methyl)-5-thia-1-aza-bicyclo[4.2.0]oct-2-ene (5 g.) m.p. 220° C (decomposition) is obtained.

$[\alpha]_D^{20} = +52.6° \pm 3.5°$ (c = 1, water).

EXAMPLE 25

Iodomethyl pivalate (5.62 g.) is added to a suspension of the potassium salt of 3-acetoxymethyl-2-carboxy-8-oxo-7-[(1,3-dithiol-2-on-4-yl)-acetamido]-5-thia-1-aza-bicyclo[4.2.0]oct-2-ene (9.9 g.) in dimethylformamide (200 cc.) cooled to 0° C. After stirring for 15 minutes at 5° C, the slightly cloudy mixture is poured into a decanting funnel containing ethyl acetate (400 cc.) and distilled water (800 cc.). The aqueous phase is washed with ethyl acetate (200 cc.) and the organic fractions are combined and then washed with water (500 cc.) and a saturated sodium bicarbonate solution (300 cc.). The organic phase is dried over sodium sulphate, treated with decolourising charcoal, filtered and then concentrated to dryness under reduced pressure (20 mm Hg).

The residue is washed with isopropyl ether (50 cc.) and filtered off. White crystals (8.7 g.) are obtained which are crystallized from ethanol (200 cc.) to give 3-acetoxymethyl-8-oxo-7-[(1,3-dithiol-2-on-4-yl)-acetamido]-2-pivaloyloxymethoxycarbonyl-5-thia-1-aza-bicyclo[4.2.0]oct-2-ene (6.1 g.) as white crystals m.p. approximately 135° C.

$[\alpha]_D^{20} = +62° \pm 1°$ (c = 1, chloroform).

EXAMPLE 26

Iodomethyl pivalate (2.66 g.) is added to a suspension of the potassium salt of 2-carboxy-3-[(2-methyl-1,3,4-thiadiazol-5-yl)-thiomethyl]-8-oxo-7-[(1,3-dithiol-2-on-4-yl)-acetamido]-5-thia-1-aza-bicyclo-[4.2.0]oct-2-ene (5.18 g.) in dimethyl formamide (100 cc.) cooled to 0° C. The reaction mixture is stirred for 10 minute at 5° C; it becomes limpid and is poured into a decanting funnel containing ethyl acetate (100 cc.) and water (200 cc.). The organic phase is washed with a saturated sodium bicarbonate solution (100 cc.) and then with a saturated sodium chloride solution (100 cc.). The organic phase is dried over sodium sulphate, treated with decolourising charcoal, filtered and concentrated to dryness under reduced pressure (20 mm Hg). The residue (5 g.) is chromatographed on silica (80 g.). A product (4.5 g.) is eluted with a 70-30 by volume mixture of ethyl acetate and cyclohexane, and is crystallised from a mixture of ethyl acetate and cyclohexane (50-50 by volume) (60 cc.). 3-[(2-Methyl-1,3,4-thiadiazol-5-yl)-thiomethyl]-8-oxo-7-[(1,3-dithiol-2-on-4-yl)-acetamido]-2-pivaloyloxymethoxycarbonyl-5-thia-1-aza-bicyclo[4.2.0]oct-2-ene (3 g.) is thus obtained as white crystals m.p. approximately 110° C. $[\alpha]_D^{20} = -85° \pm 1.5°$ (c = 1, chloroform).

EXAMPLE 27

A solution of iodomethyl pivalate (8.65 g.) in dimethylformamide (70 cc.) is added to a solution of the sodium salt of 2-carboxy-3-[(1-methyl-1,2,3,4-tetrazol-5-yl)-thiomethyl]-8-oxo-7-[(1,3-dithiol-2-on-4-yl)-acetamido]-5-thia-1-aza-bicyclo[4.2.0]oct-2-ene (18.2 g.) in dimethylformamide (115 cc.) over the course of 15 minutes, whilst maintaining the temperature at 5° C. The mixture is allowed to react for 1 hour at 5° C and is then concentrated to dryness under reduced pressure (0.5 mm Hg). The residue is taken up in ethyl acetate (500 cc.). The mixture is washed successively with water (600 cc.), a saturated aqueous sodium bicarbonate solution (500 cc.) and water (900 cc.). It is dried over sodium sulphate and concentrated to dryness under reduced pressure (20 mm Hg). The residue obtained is chromatographed on silica (450 g.), elution being carried out successively with a mixture of cyclohexane and ethyl acetate (6/4 by volume) (1 liter) and then with a mixture of cyclohexane and ethyl acetate (4/6 by volume) (4 liters). The eluates are concentrated to dryness under reduced pressure (20 mm Hg). A residue (12.7 g.) is obtained in the form of a frothy solid which is crystallised from a mixture of ethyl acetate and ether (1/1 by volume) (120 cc.). A white crystalline product (7.4 g.) is obtained, which when dried at 30° C under 0.5 mm Hg retains about 3% of ethyl acetate. The product is treated overnight with water (250 cc.) while stirring and the crystals are filtered off and then dried (35° C-0.5 mm Hg). 3-[(1-Methyl-1,2,3,4-tetrazol-5-yl)-thiomethyl]-8-oxo-7-[(1,3-dithiol-2-on-4-yl)-acetamido]-2-pivaloyloxymethoxycarbonyl-5-thia-1-aza-bicyclo[4.2.0]oct-2-ene (6.6 g.), m.p. 100° C is thus obtained. $[\alpha]_D^{20} = -21.6° \pm 0.8°$ (c = 1, dimethylformamide).

EXAMPLE 28

The sodium salt of 2-carboxy-3-[(1-methyl-1,2,3,4-tetrazol-5-yl)-thiomethyl]-9-oxo-7-[(1,3-dithiol-2-on-4-yl)acetamido]-5-thia-1-aza-bicyclo[4.2.0]oct-2-ene (5.08 g.) is dissolved in dimethylformamide (100 cc.) at 5° C. A solution of iodomethyl acetate (2 g.) in dimethylformamide (10 cc.) is added to this solution and the reaction mixture is stirred for 10 minutes at 5°. It is then poured into water (500 cc.) and extracted twice with ethyl acetate (200 cc.). The combined organic phases are washed with water (100 cc.), saturated sodium bicarbonate solution (100 cc.), a 5% sodium bisulphite solution (100 cc.) and a saturated sodium chloride solution (100 cc.). The organic phase is dried over magnesium sulphate, filtered in the presence of decolourising charcoal and concentrated to dryness under reduced pressure (15 mm Hg). This gives a white product (5 g.) which is recrystallised from acetonitrile (50 cc.). 2-Acetoxymethoxycarbonyl-3-[(1-methyl-1,2,3,4-tetrazol-5-yl)thiomethyl]-8-oxo-7-[(1,3-dithiol-2-on-4-yl)-acetamido]-5-thia-1-aza-bicyclo[4.2.0]oct-2-ene (3 g.) is thus obtained as white crystals m.p. 154° C.

$[\alpha]_D^{20} = -27.5° \pm 1.5°$ (c = 0.5, dimethylformamide).

The present invention also provides pharmaceutical compositions which are useful for therapeutic purposes which contain, as active ingredient, at least one cephalosporin of the formula (I) associated with a pharmaceutically acceptable carrier, diluent or adjuvant. These compositions can be administered orally, parenterally or rectally.

Tablets, pills, powders or granules can be used as solid compositions for oral administration. In these compositions, an active ingredient of the present invention is mixed with one or more inert diluents or adjuvants such as sucrose, lactose or starch. These compositions can also contain substances other than the diluents, for example a lubricant such as magnesium stearate.

Pharmaceutically acceptable emulsions, solutions, suspensions, syrups or elixirs contaning an inert diluent, such as water or paraffin oil, can be used as liquid compositions suitable for oral administration. These compounds can also contain substances other than the diluents, for example adjuvants such as wetting agent, sweeteners or flavouring substances.

The compositions for parenteral administration can be sterile, aqueous or non-aqueous solutions, suspensions or emulsions. As the solvent or vehicle it is possible to use propylene glycol or polyethylene glycol, vegetable oils, in particular olive oil, and injectable organic esters, for example ethyl oleate. These compositions can also contain adjuvants, in particular wetting agents, emulsifiers or dispersing agents. Sterilisation can be carried out in various ways, for example by a bacteriological filter, by incorporating sterilising agents into the composition, by irradiation or by heating. These compositions can also be prepared in the form of solid sterile compositions which can be dissolved, at the time of use, in sterile water or any other suitable injectable medium.

The compositions for rectal administration are suppositories which in addition to the active product can contain excipients such as cacao butter or suppositories wax.

In human therapy, the compositions according to the present invention are particularly useful in the treatment of infections of bacterial origin.

The posology most suitable will normally be decided by the Doctor, taking into consideration age, weight, degree of infection and other factors specific to the patient to be treated. In general the doses for an adult patient are between 1 and 12 g of active ingredient per day, administered orally, intramuscularly or intravenously.

The following Examples 29 and 30 illustrate the compositions according to the present invention.

EXAMPLE 29

An injectable solution having the following composition is prepared:

| | | |
|---|---|---|
| Sodium salt of 3-[(1-methyl-1,2,3,4-tetrazol-5-yl)-thiomethyl]-2-carboxy-7-[(1,3-dithiol-2-on-4-yl)-acetamido]-8-oxo-5-thia-1-aza-bicyclo[4.2.0]oct-2-ene | 261.5 | mg |
| Sodium chloride | 1.6 | mg |
| Injectable solution | 2 | cc. |

EXAMPLE 30

Tablets having the following composition are prepared in accordance with conventional techniques:

| | | |
|---|---|---|
| 3-[(1-Methyl-1,2,3,4-tetrazol-5-yl)-thiomethyl]-8-oxo-7-[(1,3-dithiol-2-on-4-yl)-acetamido]-2-pivaloyloxymethoxycarbonyl-5-thia-1-aza-bicyclo[4.2.0]oct-2-ene | 308 | mg |
| Starch | 90 | mg |
| Precipitated silica | 30 | mg |
| Magnesium stearate | 5 | mg. |

We claim:
1. A cephalosporin compound of the formula:

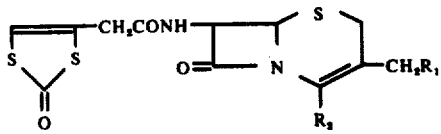

in which either (a) $R_1$ is hydrogen, acetoxy, azido, (1,2,3-thiadiazol-4-yl)-carbonylthio or heterocyclylthio selected from the class consisting of (1,3,4-thiadiazol-2-yl)-thio which is unsubstituted or substituted by straight or branched chain $C_{1-4}$ alkyl or alkoxy, straight or branched chain $C_{1-4}$ alkylthio, straight or branched chain $C_{1-4}$ alkylsulphonyl, amino or acetylamino; (1,2,3,4-tetrazol-5-yl) thio which is unsubstituted or substituted in the 1-position by straight or branched chain $C_{1-4}$ alkyl, hydroxy straight or branched chain $C_{1-4}$ alkyl, phenyl or hydroxyphenyl, or in the 2-position by straight or branched chain $C_{1-4}$ alkyl or hydroxy straight or branched chain $C_{1-4}$ alkyl; (1,2,4-triazol-3-yl)-thio; (4-methyl-1,3-thiazol-2-yl)-thio; and (3-methyl-1,2,4-thiadiazol-5-yl)-thio; and $R_2$ is carboxy or a radical of the formula:

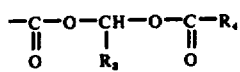

in which the radical:

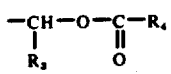

is a radical which can be easily removed enzymatically, and in which $R_3$ is hydrogen or straight or branched chain $C_{1-4}$ alkyl and $R_4$ is straight or branched chain $C_{1-4}$ alkyl or cyclohexyl; or (b) $R_1$ is the pyridinio ion and $R_2$ is the carboxylato ion; or, when $R_2$ represents carboxy, a pharmaceutically acceptable non-toxic metal salt thereof or addition salt thereof with a pharmaceutically acceptable non-toxic nitrogen-containing base.

2. A cephalosporin compound as claimed in claim 1, in which either $R_1$ is hydrogen, acetoxy, azido, (1,2,3-thiadiazol-4-yl)-carbonylthio, (1,3,4-thiadiazol-2-yl)-thio which is unsubstituted or substituted by $C_{1-2}$ alkyl, methoxy, methylthio, methylsulphonyl, amino or acetylamino; (1,2,3,4-tetrazol-5-yl)-thio which is unsubstituted or substituted in the 1-position by straight or branched chain $C_{1-4}$ alkyl, hydroxy $C_{1-2}$ alkyl or phenyl, or in the 2-position by methyl; (1,2,4-triazol-3-yl)-thio; (4-methyl-1,3-thiazol-2-yl)-thio; or (3-methyl-1,2,4-thiadiazol-5-yl)-thio, and $R_2$ is carboxy or pivaloyloxymethoxycarbonyl; or $R_1$ is the pyridinio ion and $R_2$ is the carboxylato ion, or when $R_2$ represents carboxy a pharmaceutically acceptable non-toxic metal salt thereof or addition salt thereof with a pharmaceutically acceptable non-toxic nitrogen-containing base.

3. A cephalosporin compound as claimed in claim 1, which is 3-[(1-methyl-1,2,3,4-tetrazol-5-yl)-thiomethyl]-2-carboxy-7-[(1,3-dithiol-2-on-4-yl)-acetamido]-8-oxo-5-thia-1-aza-bicyclo[4.2.0]oct-2-ene, or a pharmaceutically acceptable non-toxic metal salt thereof or addition salt with a non-toxic nitrogen containing base.

4. A cephalosporin compound as claimed in claim 1, which is 3-{[1-(2-hydroxyethyl)-1,2,3,4-tetrazol-5-yl]-thiomethyl}-2-carboxy-7-[(1,3-dithiol-2-on-4-yl)-acetamido]-8-oxo-5-thia-1-aza-bicyclo[4.2.0]oct-2-ene, or a pharmaceutically acceptable non-toxic metal salt thereof or addition salt with a non-toxic nitrogen containing base.

5. A cephalosporin compound as claimed in claim 1, which is 3-[(5-amino-1,3,4-thiadiazol-2-yl)-thiomethyl]-2-carboxy-7-[(1,3-dithiol-2-on-4-yl)-acetamido]-8-oxo-5-thia-1-aza-bicyclo[4.2.0]oct-2-ene, or a pharmaceutically acceptable non-toxic metal salt thereof or addition salt with a non-toxic nitrogen containing base.

6. A cephalosporin compound as claimed in claim 1, which is 3-[(1-methyl-1,2,3,4-tetrazol-5-yl)-thiomethyl]-2-pivaloyloxymethoxycarbonyl-7-[(1,3-dithiol-2-on-4-yl)-acetamido]-8-oxo-5-thia-1-aza-bicyclo[4.2.0]oct-2-ene.

7. A cephalosporin compound as claimed in claim 1, which is 3-[(5-methyl-1,3,4-thiadiazol-2-yl)-thiomethyl]-2-carboxy-7-[(1,3-dithiol-2-on-4-yl)-acetamido]-8-oxo-5-thia-1-aza-bicyclo[4.2.0]oct-2-ene, or a pharmaceutically acceptable non-toxic metal salt thereof or addition salt with a non-toxic nitrogen containing base.

8. A cephalosporin compound as claimed in claim 1, which is 3-(1-pyridinio-methyl)-2-carboxylato-7-[1,3-dithiol-2-on-4-yl)-acetamido]-8-oxo-5-thia-1-aza-bicyclo[4.2.0]oct-2-ene.

9. A cephalosporin compound as claimed in claim 1, which is 3-acetoxymethyl-2-carboxy-7-[(1,3-dithiol-2-on-4-yl)acetamido]-8-oxo-5-thia-1-aza-bicyclo[4.2.0]oct-2-ene, or a pharmaceutically acceptable non-toxic metal salt thereof or addition salt with a non-toxic nitrogen containing base.

10. A cephalosporin compound as claimed in claim 1, which is 2-carboxy-3-methyl-8-oxo-7-[(1,3-dithiol-2-on-4-yl)-acetamido]-5-thia-1-aza-bicyclo[4.2.0]oct-2-ene, or a pharmaceutically acceptable non-toxic metal salt thereof or addition salt with a non-toxic nitrogen containing base.

11. A cephalosporin compound as claimed in claim 1, which is 3-azidomethyl-2-carboxy-8-oxo-7-[(1,3-dithiol-2-on-4-yl)-acetamido]-5-thia-1-aza-bicyclo[4.2.0]oct-2-ene, or a pharmaceutically acceptable non-toxic metal salt thereof or addition salt with a non-toxic nitrogen containing base.

12. A cephalosporin compound as claimed in claim 1, which is 2-carboxy-8-oxo-7-[(1,3-dithiol-2-on-4-yl)-acetamido]-3-[(1,3,4-thiadiazol-2-yl)-thiomethyl]-5-thia-1-aza-bicyclo[4.2.0]oct-2-ene, or a pharmaceutically acceptable non-toxic metal salt thereof or addition salt with a non-toxic nitrogen containing base.

13. A cephalosporin compound as claimed in claim 1, which is 2-carboxy-3-[(5-ethyl-1,3,4-thiadiazol-2-yl)-thiomethyl]-8-oxo-7-[(1,3-dithiol-2-on-4-yl)-acetamido]-5-thia-1-aza-bicyclo[4.2.0]oct-2-ene, or a pharmaceutically acceptable non-toxic metal salt thereof or addition salt with a non-toxic nitrogen containing base.

14. A cephalosporin compound as claimed in claim 1, which is 2-carboxy-3-[(5-methoxy-1,3,4-thiadiazol-2-yl)-thiomethyl]-8-oxo-7-[(1,3-dithiol-2-on-4-yl)-acetamido]-5-thia-1-aza-bicyclo[4.2.0]oct-2-ene, or a pharmaceutically acceptable non-toxic metal salt thereof or addition salt with a non-toxic nitrogen containing base.

15. A cephalosporin compound as claimed in claim 1, which is 2-carboxy-3-[(5-methylthio-1,3,4-thiadiazol-2-yl)-thiomethyl]-8-oxo-7-[(1,3-dithiol-2-on-4-yl)-acetamido]-5-thia-1-aza-bicyclo[4.2.0 oct-2-ene, or a pharmaceutically acceptable non-toxic metal salt thereof or addition salt with a non-toxic nitrogen containing base.

16. A cephalosporin compound as claimed in claim 1, which is 2-carboxy-3-[(5-mesyl-1,3,4-thiadiazol-2-yl)-thiomethyl]-8-oxo-7-[(1,3-dithiol-2-on-4-yl)-acetamido]-5-thia-1-aza-bicyclo[4.2.0]oct-2-ene, or a pharmaceutically acceptable non-toxic metal salt thereof or addition salt with a non-toxic nitrogen containing base.

17. A cephalosporin compound as claimed in claim 1, which is 3-[(5-acetylamino-1,3,4-thiadiazol-2-yl)-thiomethyl]-2-carboxy-8-oxo-7-[(1,3-dithiol-2-on4-yl)-acetamido]-5-thia-1-aza-bicyclo[4.2.0]oct-2-ene, or a pharmaceutically acceptable non-toxic metal salt thereof or addition salt with a non-toxic nitrogen containing base.

18. A cephalosporin compound as claimed in claim 1, which is 2-carboxy-8-oxo-7-[(1,3-dithiol-2-on-4-yl)-acetamido]-3-[(1,2,3,4-tetrazol-5-yl)-thiomethyl]-5-thia-1-aza-bicyclo[4.2.0]oct-2-ene, or a pharmaceutically acceptable non-toxic metal salt thereof or addition salt with a non-toxic nitrogen containing base.

19. A cephalosporin compound as claimed in claim 1, which is 2-carboxy-3-[(1-ethyl-1,2,3,4-tetrazol-5-yl)-thiomethyl]-8-oxo-7-[(1,3-dithiol-2-on-4-yl)-acetamido]-5-thia-1-aza-bicyclo[4.2.0]oct-2-ene, or a pharmaceutically acceptable non-toxic metal salt thereof or addition salt with a non-toxic nitrogen containing base.

20. A cephalosporin compound as claimed in claim 1, which is 2-carboxy-8-oxo-7-[(1,3-dithiol-2-on-4-yl)-acetamido]-3-[(1-tert-butyl-1,2,3,4-tetrazol-5-yl)-thiomethyl]-5-thia-1-aza-bicyclo[4.2.0]oct-2-ene, or a pharmaceutically acceptable non-toxic metal salt thereof or addition salt with a non-toxic nitrogen containing base.

21. A cephalosporin compound as claimed in claim 1, which is 2-carboxy-8-oxo-7-[(1,3-dithiol-2-on-4-yl)-acetamido]-3-[(1-phenyl-1,2,3,4-tetrazol-5-yl)-thiomethyl]-5-thia-1-aza-bicyclo[4.2.0]oct-2-ene, or a pharmaceutically acceptable non-toxic metal salt thereof or addition salt with a non-toxic nitrogen containing base.

22. A cephalosporin compound as claimed in claim 1, which is 2-carboxy-3-[(2-methyl-1,2,3,4-tetrazol-5-yl)-thiomethyl]-8-oxo-7-[(1,3-dithiol-2-on-4-yl)-acetamido]-5-thia-1-aza-bicyclo[4.2.0]oct-2-ene, or a pharmaceutically acceptable non-toxic metal salt thereof or addition salt with a non-toxic nitrogen containing base.

23. A cephalosporin compound as claimed in claim 1, which is 2-carboxy-8-oxo-7-[(1,3-dithiol-2-on-4-yl)-acetamido]-3-[(1,2,4-triazol-3-yl)-thiomethyl]-5-thia-1-aza-bicyclo[4.2.0]oct-2-ene, or a pharmaceutically acceptable non-toxic metal salt thereof or addition salt with a non-toxic nitrogen containing base.

24. A cephalosporin compound as claimed in claim 1, which is 2-carboxy-3-[(4-methyl-1,3-thiazol-2-yl)-thiomethyl]-8-oxo-7-[(1,3-dithiol-2-on-4-yl)-acetamido]-5-thia-1-aza-bicyclo[4.2.0]oct-2-ene, or a pharmaceutically acceptable non-toxic metal salt thereof or addition salt with a non-toxic nitrogen containing base.

25. A cephalosporin compound as claimed in claim 1, which is 2-carboxy-3-[(3-methyl-1,2,4-thiadiazol-5-yl)-thiomethyl]-8-oxo-7-[(1,3-dithiol-2-on-4-yl)-acetamido]-5-thia-1-aza-bicyclo[4.2.0]oct-2-ene, or a pharmaceutically acceptable non-toxic metal salt thereof or addition salt with a non-toxic nitrogen containing base.

26. A cephalosporin compound as claimed in claim 1, which is 2-carboxy-8-oxo-7-[(1,3-dithiol-2-on-4-yl)-acetamido]-3-[(1,2,3-thiadiazol-4-yl)-carbonyl-thiomethyl]-5-thia-1-aza-bicyclo[4.2.0]oct-2-ene, or a pharmaceutically acceptable non-toxic metal salt thereof or addition salt with a nitrogen containing base.

27. A cephalosporin compound as claimed in claim 1, which is 3-acetoxymethyl-8-oxo-7-[(1,3-dithiol-2-on-4-yl)-acetamido]-2-pivaloyloxymethoxycarbonyl-5-thia-1-aza-bicyclo[4.2.0]oct-2-ene.

28. A cephalosporin compound as claimed in claim 1, which is 3-[(2-methyl-1,3,4-thiadiazol-5-yl)-thiomethyl]-8-oxo-7-[(1,3-dithiol-2-on-4-yl)-acetamido]-2-pivaloyloxymethoxycarbonyl-5-thia-1-aza-bicyclo[4.2.0]oct-2-ene.

29. A cephalosporin compound as claimed in claim 1, which is 2-acetoxymethoxycarbonyl-3-[(1-methyl-1,2,3,4-tetrazol-5-yl)-thiomethyl]-8-oxo-7-[(1,3-dithiol-2-on-4-yl)-acetamido]-5-thia-1-aza-bicyclo[4.2.0]oct-2-ene.

30. A pharmaceutical antibacterial composition which comprises, as active ingredient, a cephalosporin compound as claimed in claim 1 together with a significant amount of a pharmaceutically acceptable carrier, diluent or adjuvant.

31. A method of combating bacterial infections in mammals, which comprises administering to the mammal an amount of a cephalosporin compound as claimed in claim 1 effective to control said bacteria.

* * * * *